Figure 2D:
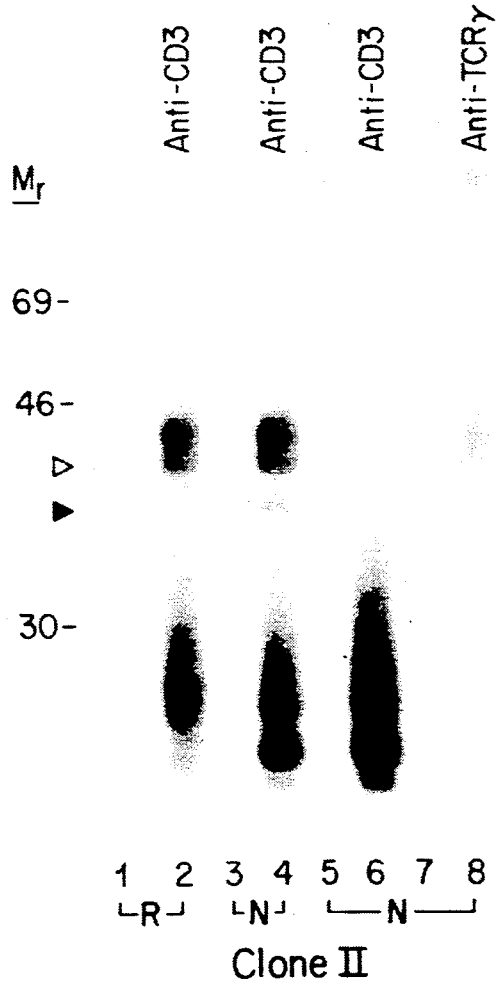

United States Patent [19]

Brenner et al.

[11] Patent Number: 5,260,223
[45] Date of Patent: Nov. 9, 1993

[54] METHODS FOR DETECTION OF HUMAN GAMMA, γ T CELL RECEPTOR

[75] Inventors: Michael B. Brenner, Ashland; Jack L. Strominger, Lexington; John G. Seidman, Milton; Stephen H. Ip, Framingham; Michael S. Krangel, Newtonville, all of Mass.

[73] Assignees: President & Fellows of Harvard College; Dana Farber Cancer Institute & T Cell Diagnostics, Inc., both of Boston, Mass.

[21] Appl. No.: 187,698

[22] Filed: Apr. 29, 1988

Related U.S. Application Data

[63] Continuation-in-part of Ser. No. 115,256, Oct. 29, 1987, Pat. No. 5,024,940, which is a continuation-in-part of Ser. No. 16,252, Feb. 19, 1987, which is a continuation-in-part of Ser. No. 882,100, Jul. 3, 1986, abandoned.

[51] Int. Cl.⁵ ............................................ G01N 33/566
[52] U.S. Cl. .................................... 436/501; 435/7.1; 435/7.24; 435/172.2; 435/240.27; 436/506; 436/518; 436/548; 436/64; 530/387.9; 530/388.22; 530/388.75; 530/350; 536/23.5
[58] Field of Search ............... 435/7, 172.2, 240.27, 435/69.6, 7.1, 7.23; 436/501, 506, 518, 548, 811, 813, 64; 530/350, 387, 395, 828, 829; 935/110

[56] References Cited

U.S. PATENT DOCUMENTS

| | | |
|---|---|---|
| 4,444,744 | 4/1984 | Goldenberg . |
| 4,550,086 | 10/1985 | Reinherz et al. ..................... 436/506 |
| 4,713,332 | 12/1987 | Mak ...................................... 435/70 |
| 4,845,026 | 7/1989 | Kung et al. ............................ 435/5 |
| 5,185,250 | 2/1993 | Brenner et al. ..................... 435/69.3 |

FOREIGN PATENT DOCUMENTS

WO87/03600 6/1987 PCT Int'l Appl. .
WO88/00209 1/1988 PCT Int'l Appl. .

OTHER PUBLICATIONS

Yoshikai et al. (1986, Nature 324:482–485).
Leiden et al. (1986, Mol. Cell. Biol. 6:3207-3214).
Quertermous et al. (1986, Nature 322:184–187).
Bank et al. (1986, Nature 322:179–181).
Lew et al. (1986 Science 234:1401-1405).
Brenner et al. (1987, Nature 325:689–694).
Brenner et al. (1987, J. Immunol. 138:1502-1509).
Petty et al. (1987, J. Biol. Chem. (262:4854–4859).
Lee et al. (1987, J. Neuroimmunol. 16:103).
Krangel and Brenner (1988, In: *The T-Cell Receptor*, Davis and Kappler (eds.), Alan R. Liss, N.Y., pp. 57–66).
Ioannides et al. (1987, Proc. Natl. Acad. Sci. U.S.A. 84:4244–4248).
Hashimoto et al. (1987, Proc. Natl. Acad. Sci. U.S.A. 84:5883–5887).
Ang et al. (1987, J. Exp. Med. 165:1453–1458).
Hata et al. (1987, Science 238:678–682).
Band et al. (1987, Science 238:682–684).
Freimark et al. (1987, J. Immunol. 138:1724–1729).
Borst et al. (1987, Nature 325:683–688).
Krangel et al. (1987, Science 237:64–67).

(List continued on next page.)

*Primary Examiner*—Robert J. Hill, Jr.
*Assistant Examiner*—Laurie Scheiner
*Attorney, Agent, or Firm*—Pennie & Edmonds

[57] ABSTRACT

The present invention provides purified polypeptides which comprise at least a portion of a δ T cell receptor polypeptide, a γ T cell receptor polypeptide, a γ, γ T cell receptor complex or a γ, δ T cell receptor complex. Substances capable of forming complexes with these polypeptides are also provided.

Additionally, methods for detecting T cells which have within them or on their surfaces a polypeptide of the present invention are provided. Moreover, methods for diagnosing immune system abnormalities are provided which comprise measuring in a sample from a subject the number of T cells which have within them or on their surfaces a polypeptide of the present invention.

48 Claims, 14 Drawing Sheets

OTHER PUBLICATIONS

Goorha et al. (1987, Proc. Natl. Acad. Sci U.S.A. 84:4547–4551).
Krangel et al. (1987, Proc. Natl. Acad. Sci. U.S.A. 84:3817–3821).
Bonneville et al. (1987, J. Cell. Biochem, Suppl. 11D, Abstract T103, p. 212).
Borst et al. (*ibid*, Abstract T104, p. 212).
Coligan et al. (*ibid*, Abstract T105, p. 212).
Federspiel et al. (*ibid*, Abstract T106, p. 213).
Jones et al. (*ibid*, Abstract T107, p. 213).
Krangel et al. (*ibid*, Abstract T108, p. 213).
Stingl et al. (*ibid*, Abstract T119, p. 217).
Van de Griend et al. (*ibid*, Abstract T120, p. 217).
Alarcon et al. (1987, Proc. Natl. Acad. Sci. U.S.A. 84:3861–3865).
Brennan et al. (1988, J. Autoimmunity 1:319–326).
Foroni et al. (1988, Blood 71:356–362).
Faure et al. (1988, J. Immunol. 140:1372–1379).
Leiden et al. (1988, Immunogenetics 27:231–238).
Groh et al. (1988, Clin. Res. 36:652A).
Faure et al. (1988, J. Immunol., 140–2128).
Allison et al., J. Immunol. 129, 2293–2300 (1982).
Kappler et al., Cell 35, 295–302 (1983).
Acuto et al., J. Exp. Med. 158, 1368–1373 (1983).
Haskins et al., J. Exp. Med. 157, 1149–1169 (1983).
Acuto et al., Cell 34, 717–726 (1983).
Samelson and Schwartz, Immunological Reviews 81, 131–144 (1984).
Hedrick et al., Nature 308, 153–158 (1984).
Yanagi et al., Nature 308, 145–149 (1984).
Saito et al., Nature 312, 36–40 (1984)
Sim et al., Nature 312, 771–775 (1984).
Chien et al., Nature 312, 31–35 (1984).
Siu et al., Cell 37, 393–401 (1984).
Patten et al., Nature 312, 40–46 (1984).
Yoshikai et al., Nature 312, 521–524 (1984).
Yanagi et al., Proc. Natl. Acad. Sci. U.S.A. 82, 3430–3434 (1985).
Hendrick et al., Proc. Natl. Acad. Sci. U.S.A. 82 531–535 (1985).
Becker et al., Nature 317, 430–434 (1985).
Tonegawa, scientific American, pp. 122–131 (Oct., 1985).
Yague et al., Cell 42, 81 14 87 (1985).
Blanckmeister et al., J. Exp. Med. 162:851–863 (1985).
Dembic et al., Nature 320, 232–238 (1986).
Saito et al., Nature 309, 757–762 (1984).
Kranz et al., Nature 313, 752–755 (1985).
Snodgrass et al., Nature 315, 232–233 (1985).
Lefranc and Rabbitts, Nature 316, 464–466 (1985).
Murre et al., Nature 316, 549–552 (1985).
Heilig et al., Nature 317, 68–70 (1985).
Hayday et al., Cell 40, 259–269 (1985).
Dialynas et al., Proc. Natl. Acad. Sci. U.S.A. 83, 2619 (1986).
Quertermous et al., Science 231, 252–255 (1986).
Iwamoto et al., J. Exp. Med. 163, 1203–1212 (1986).
Zauderer et al., J. Exp. Med. 163, 1314–1318 (1986).
Caccia et al., Cell 37, 1091–1099 (1984).
Kranz et al., Science 227, 941–944 (1985).
Brenner et al., J. Exp. Med. 160, 541–551 (1984).
Spits et al., J. Immunol. 135, 1922–1928 (1985).
Reinherz et al., Cell 30, 735–743 (1982).
Borst et al., J. Biol. Chem. 258, 5135–5141 (1983).
Reinherz et al., Proc. Natl. Acad. Sci. U.S.A. 80, 4104–4108 (1983).
Meuer et al., J. Exp. Med. 157, 705–719 (1983).
Oettgen et al., J. Biol. chem. 259, 12039–12048 (1984).
Weiss and Stobo, J. Exp. Med. 160, 1284–1299 (1984).
Allison and Lanier, Nature 314, 107–109 (1985).
Brenner et al., Cell 40, 183–190 (1985).
Van den Elsen et al., Proc. Natl. Acad. Sci. U.S.A. 82, 2920–2924 (1985).
Ohashi et al., Nature 316, 606–609 (1985).
Krawinkel et al., Cold Spring Harb. Symp. Quant. Biol 4, 285–294 (1976).
Binz and Wigzell, Cold Spring Harb. Symp. Quant. Biol. 4, 275–284 (1976).
Binz and Wigzell, J. Exp. Med. 154, 1261–1278 (1981).
Kung et al., Int. J. Dermat. 22, 67–73 (1983).
Krensky and Clayberger, Transplantation 39(4):339–348 (1985).
de la Hera et al., Proc. Natl. Acad. Sci. U.S.A. 82, 6268–6271 (1985).
Levin, L. S., et al., J. Pediatrics 90(1), 55–61 (1977).
Griscelli et al., (1980), in Primary Immunodeficiencies, Seligmann, M. and Hitzig, W. H., eds., Elsevier/North-Holland, pp 499–503.

(List continued on next page.)

OTHER PUBLICATIONS

Hadam, et al., (1984), in Progress in Immunodeficiency Research and Therapy I, Griscelli, C. and Vossen, J., eds., Elsevier Science Publishers B.V., pp. 43–50.
Chan and Takei, J. Immunol. 136(4), 1346–1353 (1986).
Kung et al., U.S. Pat. No. 4,614,720, filed Oct. 4, 1982.
Pardoll et al., Faseb J. 1:103–109 (1987).
Reilly et al., Nature 321:878–880 (Jun. 1986).
Rupp et al., Nature 321:876–878 (Jun. 1986).
Haars et al., J. Exp. Med. 164:1–24 (Jul. 1986).
Moingeon et al., Nature 323:638–640 (Oct. 1986).
Jones et al., Nature 323:635–638 (Oct. 1986).
Lanier and Weiss, Nature 324:268 (1986).
LeFranc et al., Proc. Natl. Acad. Sci. U.S.A. 83:9596–9600 (1986).
European Patent Application No. 200,350, published Nov. 5, 1986.
MacLeod et al., Proc. Natl. Acad. Sci. U.S.A. 83:6989–6993 (1986).
Brenner et al., Nature (London) 322:145–149 (1986).
Van Den Elsen et al., Proc. Natl. Acad. Sci. U.S.A. 83:294–2948 (1986).
Tunnacliffe et al., EMBO J. 5:1245–1252 (1986).
LeFranc et al., Cell 45:237–246 (1986).
Royer et al., J. Exp. Med. 160:947–952 (1984).
Kyte and Doolittle, J. Med. Biol. 157:105–132 (1982).
Hopp and Woods, Proc. Natl. Acad. Sci. U.S.A. 78:3824–3828 (1981).
Weiss et al, PNAS USA, vol. 83, Sep. 1986, pp. 6998–7002.
Pardoll et al, FASEB J., vol. 1, 1987, pp. 103–109.
Moingeon et al, Nature, vol. 323, Oct. 1986, pp. 638–640.
Brenner et al, Nature, vol. 322, Jul. 1986, pp. 145–149.

FIG.1A

FIG.1B

```
TGACTGGCATGAGGAAGCTACACTCCTGAAGAAACCAAAGGCTTACAAAAATGCATCTCCTTGGCTTCTGACTTCTTTGTGATTCAAGTGACCTGTCATAGCCTTGTAAAATGGCTG

CTAGCAAACCAATTTTCTTCAAAGACAACAAACCCAGCTCATCTCCAGCTTGATGGGAAGACAAAAGTCTGGGGAAGGGGGTTATGTCCTAACTGCTTTGTATGCTGTTTTATA

AAGGGATAGAAGGATATAAAAAGATATAGGACTCTCTTTTTTACTCCTACAAGTGATACACTTTGAAAATGATGTTTGTCTTTTGACTTCTTTTACTTTTGAAGTAGAAAGTGGGA

ACCAACAGGTTCACAGCTTCATTCCTCCTCATGAGGAAAATAGGCCTTGGGAGAAGAAGAGCGGTGCCCTTTATCTAAACATGGAAGGCTCTGCTCAACTGAGCACTAGATTGCTACAA

ACCAGCATCATCTTCTCCTCCTGTCCTCACGGCTTGTCCACCCCTCTATGTTCACTTCAGGAGCCACACTAGAGATTCTGCATGGCGTGGAGGAGGACAAAGTTCCAGCACTTTCTGC

CTCTCCTAATACTTTACAAATGAGATTACATTTGCTAATACTTTATGAGCAGCAATGAGGTTCCAAAATCTCATCTAAATACTCTCCAATCTATTAGCAAAAATCAGAGTA

AAATACAGAGGAAAGGCACTGCTCTTTCTGTTAATTGATTAACATGCATGAATTAGCTCCCTCTGAGTTCCAGGCACTATGCTGAGAGTACAAAGAAGACACAAGTCTGCTTTCAAGCAA

CTCACTGTGAAAGTGTTTTGAAGGGAGGAACAGAAATGAGACCCCTATCTTTTACTGTCTTTGCCTGCCAATCTGTATTTGAAACCATTGGACACTG

ATTCTCTCTGGGACTTTGGCATGATGGTTTTCTGCCTTTCTTCTCTCAGCCTCTGCCTCTATTGCATTTATTAAACTGCATTGTGTGCAAAAAAAAAAAAAA
```

FIG. 1C

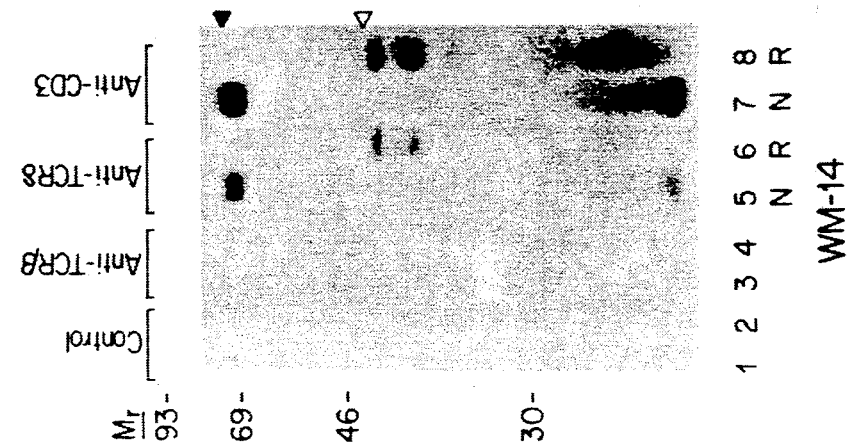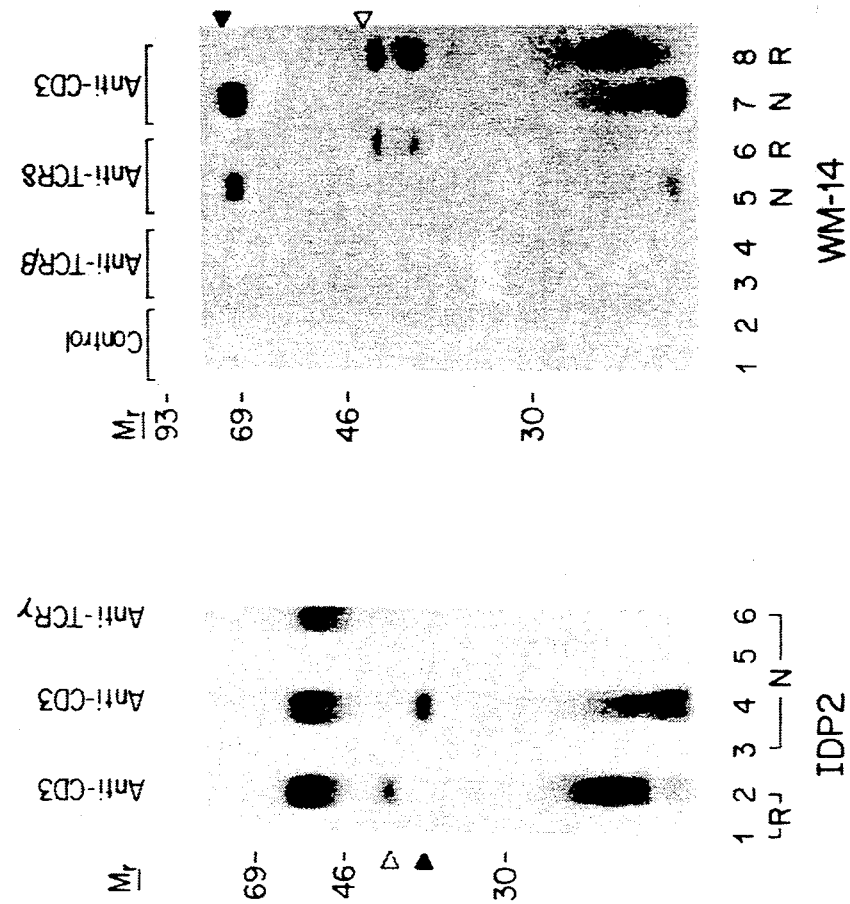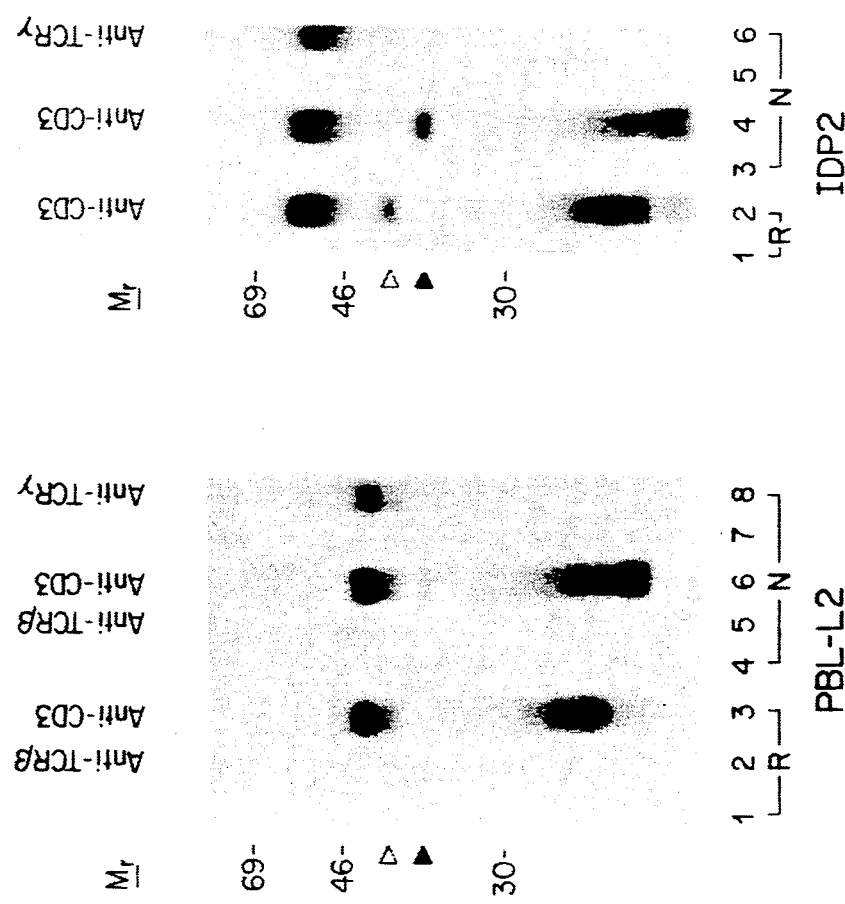

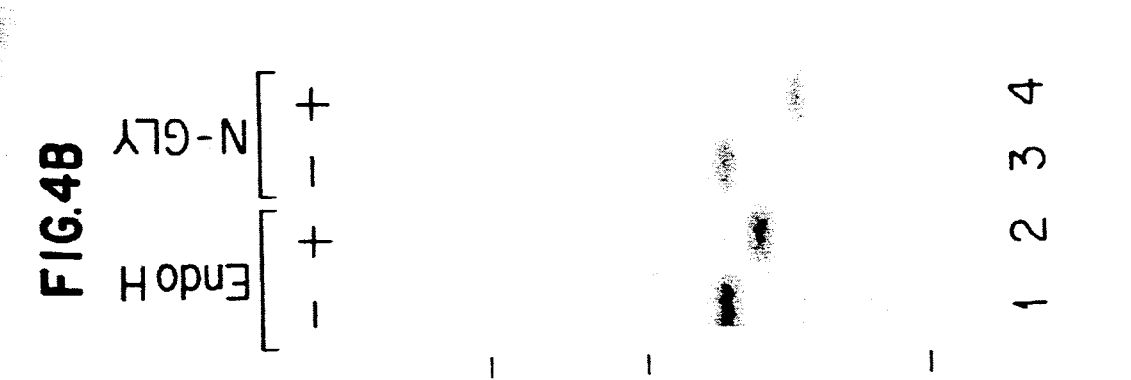
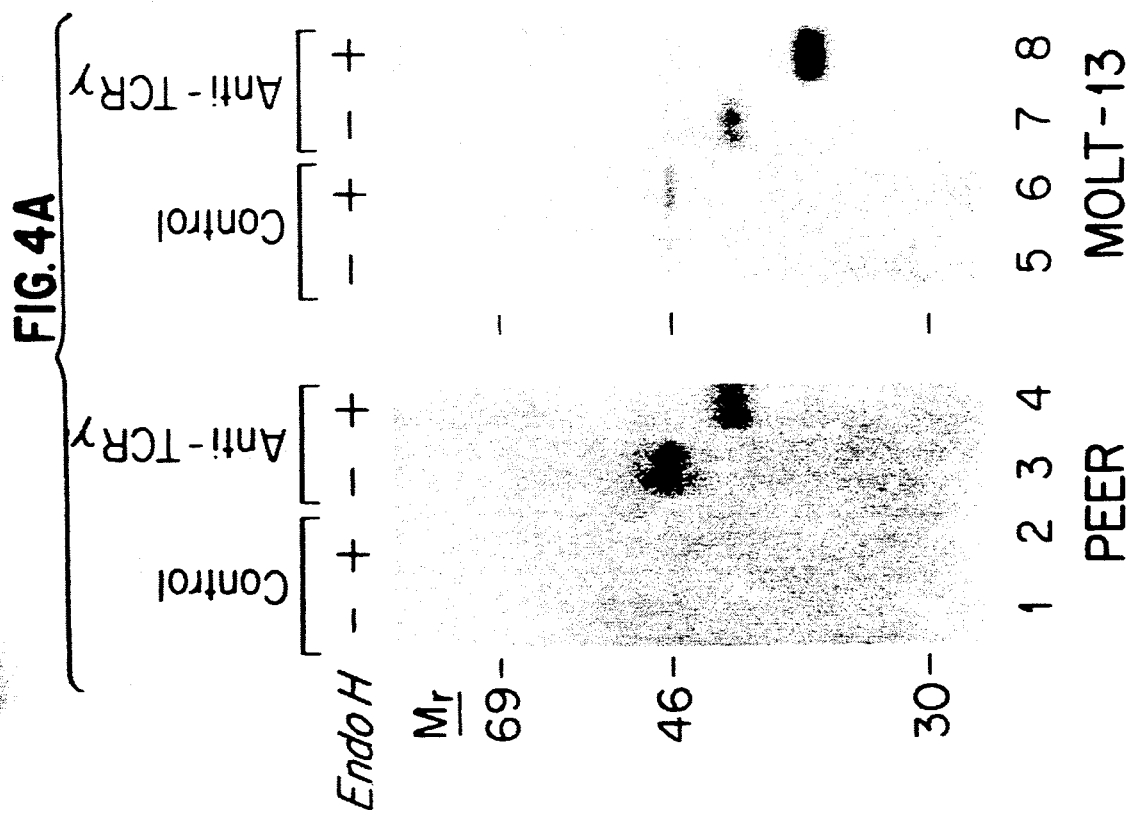

```
                                                                              →V
                                                               TCT CCT GCC AGT CAG
                                                               S   P   A   S   Q

TTC CTG
                                                   F   L

CTA GTG GTG CTT
                                               L   V   V   L

GCC
                                           A
                                      →B
                                   TGG
                                   W

ATG CGG
                                M   R

1 TGGTCCCTTTCCTTCCAAGGCCCCGAGAGGAAGC
```

```
 88 AAA TCT TCC AAC TTG GAA GGG AGA ACG AAG TCA GTC ACC AGG CAG ACT GGG TCA TCT GCT GAA ATC ACT TGC GAT CTT ACT GTA ACA
    K   S   S   N   L   E   G   R   T   K   S   V   T   R   Q   T   G   S   S   A   E   I   T   C   D   L   T   V   T

175 AAT ACC TTC TAC ATC CAC TGG TAC CTA CAC CAG GAG GGG AAG GCC CCA CAG CGT CTT CTG TAC TAT GAC GTC TCC ACC GCA AGG GAT
    N   T   F   Y   I   H   W   Y   L   H   Q   E   G   K   A   P   Q   R   L   L   Y   Y   D   V   S   T   A   R   D

262 GTG TTG GAA TCA GGA CTC AGT CCA GGG AAG TAT TAT ACT CAT ACA CCC AGG AGG TGG AGC TGG ATA TTG AGA CTG CAA AAT CTA ATT
    V   L   E   S   G   L   S   P   G   K   Y   Y   T   H   T   P   R   R   W   S   W   I   L   R   L   Q   N   L   I
                                                                                →N
349 GAA AAT GAT TCT GGG GTC TAT TAC TGT GCC ACC TGG GAC AGG CCC CGC CTT AAG AAA CTC TTT GGC AGT GGA ACA ACA CTT GTT GTC
    E   N   D   S   G   V   Y   Y   C   A   T   W   D   R   P   R   L   K   K   L   F   G   S   G   T   T   L   V   V
        →C1
436 ACA GAT AAA CAA CTT GAT GCA GAT GTT TCC CCC AAG CCC ACT ATT TTT CTT CCT TCG ATT GCT GAA ACA AAA CTC CAG AAG GCT GGA
    T   D   K   Q   L   D   A   D   V   S   P   K   P   T   I   F   L   P   S   I   A   E   T   K   L   Q   K   A   G
                                                                      →J
```

FIG.5B

```
523
ACA TAC CTT TGT CTT CTT GAG AAA TTT TTC CCA GAT ATT ATT AAG ATA CAT TGG CAA GAA AAG AAG AGC AAC ACG ATT CTG GGA TCC
 T   Y   L   C   L   L   E   K   F   F   P   D   I   I   K   I   H   W   Q   E   K   K   S   N   T   I   L   G   S

610
CAG GAG GGG AAC ACC ATG AAG ACT AAC GAC ACA TAC ATG AAA TTT AGC TGG TTA ACG GTG CCA GAA GAG TCA CTG GAC AAA GAA CAC
 Q   E   G   N   T   M   K   T   N   D   T   Y   M   K   F   S   W   L   T   V   P   E   E   S   L   D   K   E   H
                                ──────                                                              ───────►CIIb
697
AGA TGT ATC GTC AGA CAT GAG AAT AAC AAG AAT GGA ATT GAT CAA GAA ATT ATC TTT CCT CCA ATA AAG ACA GAT GTC ACC ACA GTG
 R   C   I   V   R   H   E   N   N   K   N   G   I   D   Q   E   I   I   F   P   P   I   K   T   D   V   T   T   V

784
GAT CCC AAA TAC AAT TAT TCA AAG GAT GCA AAT GAT GTC ATC ACA ATG GAT CCC AAA GAC AAT TGG TCA AAA GAT GCA AAT GAT ACA
 D   P   K   Y   N   Y   S   K   D   A   N   D   V   I   T   M   D   P   K   D   N   W   S   K   D   A   N   D   T
                       ─────                                      ─────►CIIc                      ─────
871
CTA CTG CTG CAG CTC ACA AAC ACC TCT GCA TAT TAC ACG TAC CTC CTC CTC CTC CTC AAG AGT GTG GTC TAT TTT GCC ATC ATC ACC
 L   L   L   Q   L   T   N   T   S   A   Y   Y   T   Y   L   L   L   L   L   K   S   V   V   Y   F   A   I   I   T
          ─────►CIII         ─────
958
TGC TGT CTG CTT AGA AGA ACG GCT TTC TGC TGC AAT GGA GAG AAA TCA TAA CAGACGGTGGCACAAGGAGGCCATCTTTTCCTCATCGGTTATTGTCC
 C   C   L   L   R   R   T   A   F   C   C   N   G   E   K   S   U

1056
CTAGAAGCGTCCCGAATTCAAGGT
```

FIG.5C

METHODS FOR DETECTION OF HUMAN GAMMA, γ T CELL RECEPTOR

This invention was supported by several NIH grants, and the Government has certain rights to the invention.

This application is a continuation-in-part of U.S. Pat. application Ser. No. 115,256, filed Oct. 29, 1989, now U.S. Pat. No. 5,024,940, issued Jun. 18, 1991, which is a continuation-in-part of Ser. No. 016,252, filed Feb. 19, 1987, which is a continuation-in-part of Ser. No. 882,100 filed Jul. 3, 1986, each of which is incorporated by reference herein in its entirety.

1. INTRODUCTION

The present invention is directed to purified polypeptides which comprise at least a portion of a δTCR polypeptide, a γTCR polypeptide, or a γ, δTCR complex. The invention is also directed to substances capable of forming complexes with these polypeptides. In addition, methods for detecting T cells which have within them or on their surfaces a polypeptide of the present invention are provided and may be used for diagnosing immune system abnormalities.

2. BACKGROUND OF THE INVENTION

Understanding T cell recognition of antigen and the restriction of the process by major histocompatibility complex (MHC) encoded antigens has been an important goal in immunology. A major step forward occurred with the immunochemical identification of clone specific disulfide-linked heterodimers on T cells, composed of subunits termed T cell antigen receptors (TCR) α and β. The α and βTCR subunits have a relative molecular mass ($M_r$) of approximately 50,000 and 40,000 daltons, respectively (Allison et al., 1982, Immunol. 129:2293-2300; Meuer et al., 1983, J. Exp. Med. 157:705-719; Haskins et al., 1983, J. Exp. Med. 157:1149-1169). Genes that rearrange during T cell ontogeny and encode the βTCR (Yanagi et al., 1984, Nature 308:145-149; Hedrick et al., 1984, Nature 308:153-158) and αTCR (Chien et al., 1984, Nature 312:31-35; Scito et al., 1984, Nature 312:36-40, Sim et al., 1984, Nature 312:771-775) subunits were isolated either by subtractive hybridization or by probing with oligonucleotides.

A unique feature of the human α,βTCR was the observed comodulation (Meuer et al., 1983, J. Exp. Med. 157:705-719), coimmunoprecipitation (described in copending application Serial No. 882,100 filed Jul. 7, 1986, which is incorporated by reference in its entirety; Oettgen, et al., 1984, J. Biol. Chem. 259:12,039-12,048) and required coexpression (Weiss et al., 1984, J. Exp. Med. 160:1284-1299) of the α,βTCR molecules with the T3 glycoprotein, which suggested that these two structures were related. Subsequently, the direct physical association of the two protein complexes was demonstrated by chemically cross-linking the α,βTCR molecules to the T3 glycoprotein and identifying the components of the cross-linked complex as the TCR subunit and the T3 glycoprotein ($M_r$28,000) subunit (Brenner et al., 1985, Cell 40:183-190). A T3 counterpart is similarly associated with murine α,βTCR (Allison et al., 1985, Nature 314:107-109; Samelson et al., 1984, Immunol. Rev. 81:131-144).

A third gene that rearranges in T cells, designated γTCR, has been identified in mouse (Saito et al., 1984, Nature 309:757-762; Kranz et al., 1985, Nature 313:752-755; Hayday et al., 1985, Cell 40:259-269) and in man (Lefranc et al., 1985, Nature 316:464-466; Murre et al., 1985, Nature 316:549-552). However, there are major differences between the human and mouse γTCR gene in terms of its genetic structure; for example, the cDNA of a human Cγ2 gene indicates five potential sites for N-linked glycosylation in the γTCR gene product, which contrasts with the notable absence of such sites in certain murine γTCR gene sequences. Thus, certain human γTCR gene products have a higher molecular weight than that of certain murine TCRγ proteins.

The γTCR gene rearrangements occur in lymphocytes with suppressor-cytotoxic as well as helper phenotypes and may produce a large number of γTCR chains (Lefranc et al., 1985, Nature 316:464-466; Murre et al., 1985, Nature 316:549-552; Quertermous et al., 1986, Science 231:252-255; LeFranc et al., 1986, Cell 45:237-246, Iwamoto et al., 1986, J. Exp. Med. 163:1203-1212; Zauderer et al., 1986, J. Exp. Med. 163:1314-1318). However, the function of the γTCR gene is unknown. Furthermore, neither the protein encoded by the γTCR gene nor its possible association with other structures (as ogccurs with α,βTCR and T3 glycoproteins) have been defined. In humans, the multiple glycosylation sites render it impossible to predict with accuracy the nature and size of the γTCR polypeptide structure. Additionally, the published literature does not teach or suggest the utility of γTCR with regard to diagnosing, monitoring or staging human diseases.

It appears increasingly likely that the α,βTCR molecule alone determines both antigen recognition and MHC restriction on at least some T cells (Yague et al., 1985, Cell 42:81-87; Dembic et al., 1986, Nature 320:232-238). However, it is not clear that α,βTCR accounts for the process of T cell selection during T cell ontogeny or for all antigen specific recognition by mature T cells. For example, suppressor T lymphocytes remain an enigma; in some cases they delete or fail to rearrange TCR genes (Hedrick et al., 1985, Proc. Natl. Acad. Sci. U.S.A. 82:531-535; Blanckmeister et al., 1985, J. Exp. Med. 162:851-863). Thus, it is of great importance to determine if a second TCR exists, to define its structure (particularly with regard to the possible use of the γTCR gene product) and ultimately to understand what function or functions it serves.

3. SUMMARY OF THE INVENTION

The present invention provides a purified polypeptide which comprises at least a portion of a δTCR polypeptide. The δTCR polypeptides of the invention may comprise at least a portion of the primary amino acid sequence shown in FIG. 1. Additionally, a substance capable of specifically forming a complex with at least one δTCR polypeptide is provided.

A purified polypeptide which comprises at least a portion of a γTCR polypeptide is also provided by the present invention. In one embodiment of the invention the γTCR polypeptide has a molecular weight of about 40,000 daltons (Form 1). In another embodiment of the invention the γTCR polypeptide has a molecular weight of about 55,000 daltons (Form 2abc). Form 2abc γTCR polypeptide has a slightly larger peptide backbone and contains one extra potential N-linked glycan than Form 1 γTCR polypeptide. Form 1 and Form 2abc γTCR polypeptides are more fully described in copending application Serial Nos. 882, 100 filed Jul. 3, 1986 and 016,252 filed Feb. 19, 1987, which are incorporated by reference in their entirety. In yet another embodiment of the invention the γTCR polypeptide has a molecular weight of about 40,000 daltons (Form 2bc). Form 2bc γTCR polypeptide possesses a slightly smaller peptide backbone and 2-3 less potential N-linked glycans. Form 2bc γTCR polypeptide may comprise any portion of the primary amino acid sequence of the γTCR polypeptide shown in FIG. 5. Additionally, the γTCR polypeptide may be a human γTCR polypeptide.

The present invention further provides a purified complex which comprises two γTCR polypeptides of the present invention associated with each other. In one embodiment of the invention, the two γTCR polypeptides are associated with each other through at least one interchain, covalent, disulfide linkage. In another embodiment of the invention, the two γTCR polypeptides are noncovalently associated with each other. In still another embodiment of the invention, the two γTCR polypeptides have the same constant domain. In yet a further embodiment of the invention, the two γTCR polypeptides have different constant domains.

The present invention also provides a substance capable of specifically forming a complex with at least one γTCR polypeptide. In one embodiment of the invention, the substance is capable of specifically forming a complex with one γTCR polypeptide. In another embodiment of the invention, the substance is capable of specifically forming a complex with more than one γTCR polypeptide. The substance may be an antibody. In one embodiment of the invention, the antibody is a polyclonal antibody. In another embodiment of the invention, the antibody is a monoclonal antibody.

The invention further provides a purified complex which comprises at least a portion of a δTCR polypeptide and at least a portion of a γTCR polypeptide herein referred to as a γ,δTCR complex. Also provided are substances capable of specifically forming a complex with at least one γ, δTCR complex. These may be used to detect T cells, each of which has a γ,δTCR complex. The γ,δTCR complexes may be present on the surface of the T cells. Alternatively, the γ,δTCR complexes may be present in the cytoplasm of the T cells.

The invention is also directed to methods for detecting the TCR polypeptides in samples including but not limited to lymphoid tissue, bone marrow, blood, peripheral blood lymphocytes, epithelial cells and the like, as well as methods for diagnosing immune abnormalities in animals and humans.

4. DESCRIPTION OF FIGURES

Figure 1B:
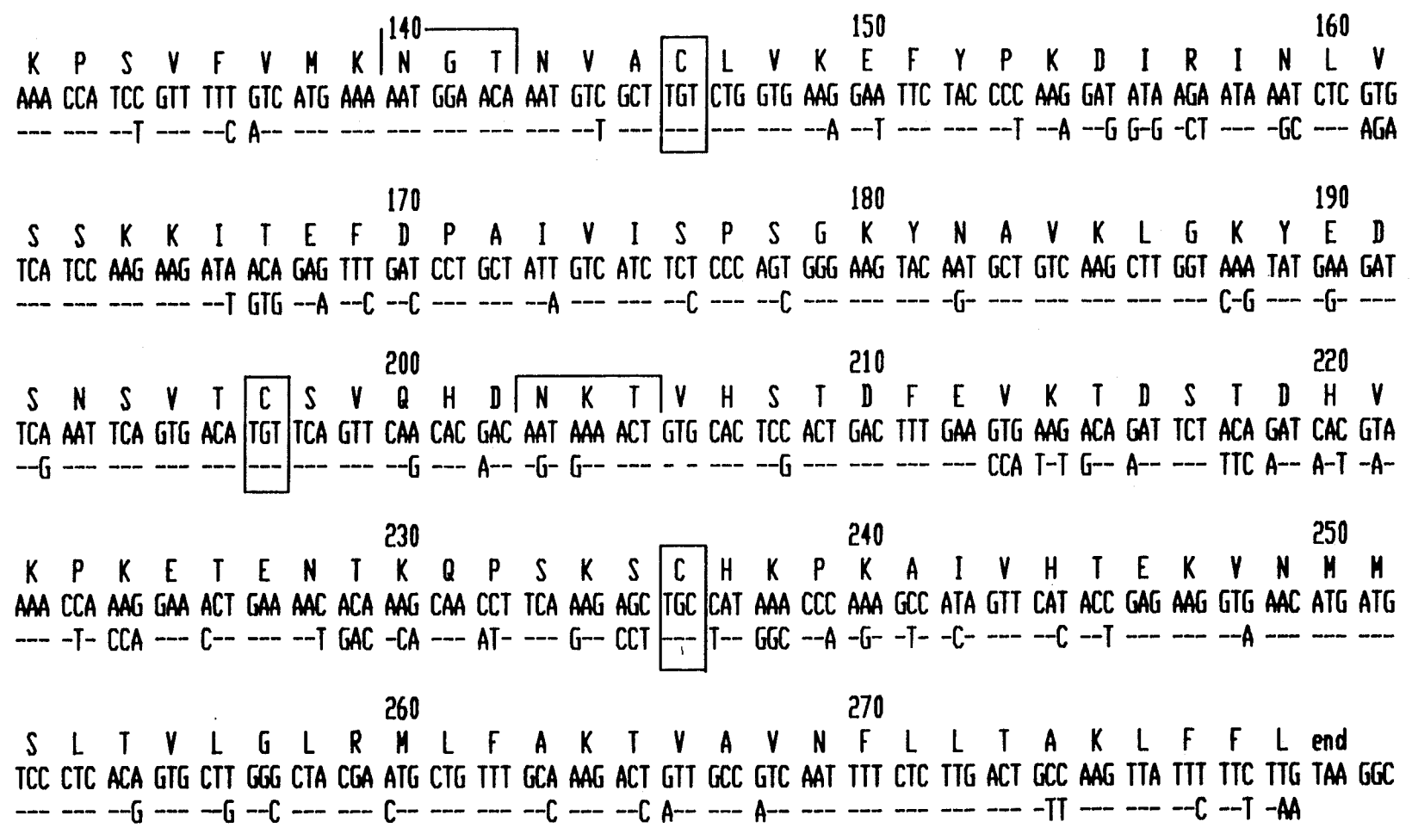

FIG. 1A–1C. Composite nucleotide sequence of group 0 cDNA clones encoding δTCR protein.

Amino acid residues are numbered from the presumed amino terminal processing point. Cysteine residues are boxed, potential N-linked glycosylation sites are bracketed, and polyadenylation signals used in the clones are underlined. The composite nucleotide sequence is compared with that of the coding region of murine cDNA clone DN-4 (Chien, et al., 1987, Nature 327:677). (—) denotes identity and (*) denotes a gap.

FIGS. 2A–2E. Immunoprecipitation of the three forms of γ,δTCR. For parts 2A–E, the antibodies used for immunoprecipitation are anti-Leu4 (anti-CD3), βF1 (anti-TCRβ), anti-δ1TCR (anti-δTCR), anti-Cγb serum (anti-γTCR) and P3 (unlabelled lanes, control). Immunoprecipitations from $^{125}$I-labelled cell lysates were analyzed by SDS-PAGE (10% polyacrylamide) under reducing (R) or nonreducing (N) conditions. An open arrow ( ) indicates the position of TCR δ under reducing condition whereas the solid arrow ( ) denotes the position of δTCR under nonreducing conditions. Size markers, $M_r$ in thousands, are shown on the left.

2A) Nondisulfide-linked γTCR (40kD) on PBL-L2. In lanes 1–6 the radiolabelled cells were solubilized in 0.3% CHAPS detergent which preserves the TCR-CD3 association, whereas in lanes 7 and 8, immunoprecipitations were performed after chain separation (see methods).

2B) Nondisulfide-linked γTCR (55kD) on IDP2 cells. In lanes 1–4 radiolabelled cells were solubilized in 0.3% CHAPS detergent, whereas in lanes 5 and 6 imunoprecipitations were carried out after chain separation.

2C) Disulfide-linked γTCR (40kD) on WM-14 cells. All lanes correspond to immunoprecipitations from 1% digitonin solubilized radiolabelled cells.

2D) Nondisulfide-linked γTCR (40kD) on thymic Clone II cells. Radiolabelled cells were solubilized in 1% digitonin (lanes 1–4) or in 0.1% Triton X-100 (lanes 5 and 6), whereas in lanes 7 and 8 immunoprecipitations were carried out after chain separation.

2E) Nondisulfide-linked γTCR (40kD) on MOLT-13 leukemia T cells. In lanes 1–4 immunoprecipitations were carried out after solubilization of cells in 0.3% CHAPS detergent, whereas in lanes 5 and 6 immunoprecipitations were carried out after chain separation.

Figure 3:
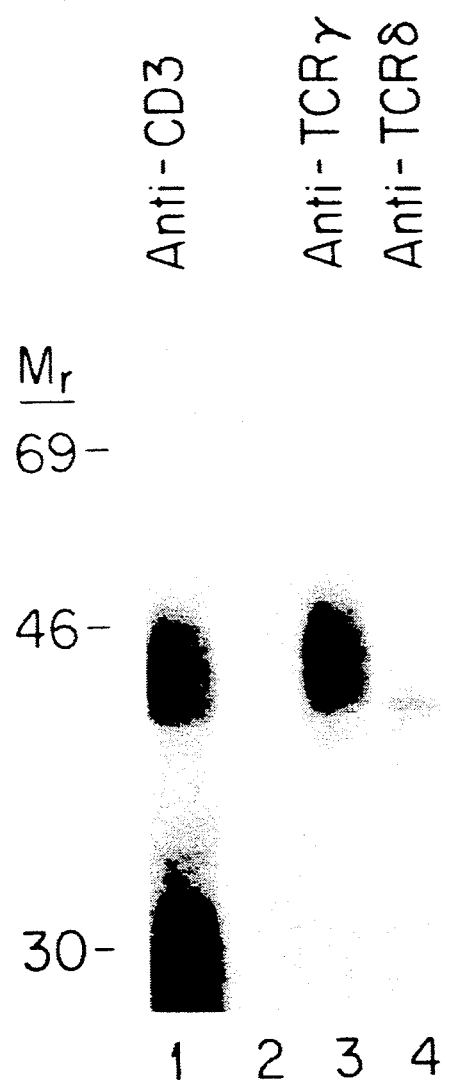

FIG. 3. Immunoprecipitation of γTCR and δTCR chain by anti-Cγml antibody and anti-TCRδI antibody, respectively. Cell surface radiolabelled MOLT-13 cells were solubilized in 0.3% CHAPS detergent and the γ, δTCR-CD3 complex was isolated with anti-CD3 monoclonal antibody. Immunoprecipitates were analyzed by 10% SDS-PAGE under reducing conditions.

Lane 1: Immunoprecipitation with anti-Leu4 (anti-CD3) mAb

Lane 3: Immunoprecipitation with anti-Cγml (anti-TCRγ) mAb after separating chains of isolated γ, δTCR-CD3 complexes.

Lane 4: Immunoprecipitation with anti-TCR δ1 (anti-TCRδ) mAb after separating chains of isolated γ, δTCR-CD3 complexes.

FIGS. 4A–4B. Determination of peptide backbone sizes and glycosylation of γ and δTCRs from PEER and MOLT-13 cells. Monoclonal antibodies used for immunoprecipitation are anti-Cγml (anti-TCRγ), anti-TCRδ1 (anti-TCRδ) and P3 (labelled control) as shown at the top of each lane. The labelled cell lines used are shown at the bottom of each 10% SDS-PAGE autoradiograph or fluorograph. All samples were resolved under reducing conditions. Size markers, $M_r$ in the thousands.

4A) Peptide backbone sizes of γTCR from PEER and MOLT-13 cells. Cells were biosynthetically labelled with $^{35}$S-cysteine and $^{35}$S-methionine for 15 minutes. Samples were either treated with Endo H (+) or mock treated (—). Immunoprecipitation with anti-Cγml shows the positions of immature γTCR of PEER cells (lane 3) and of MOLT-13 cells (lane 7), while the corresponding polypeptide backbone sizes are visualized after treatment with endo H (lanes 4 and 8).

4B) Glycosylation of TCR δ from MOLT-13 cells. $^{125}$I-labelled cells were immunoprecipitated with anti-CD3 mAb and the δTCR polypeptides were gel purified (see methods) before incubation with N-glycanase (lane 4), endo H (lane 2), or mock treated (lanes 1, and 3).

Figure 5A:
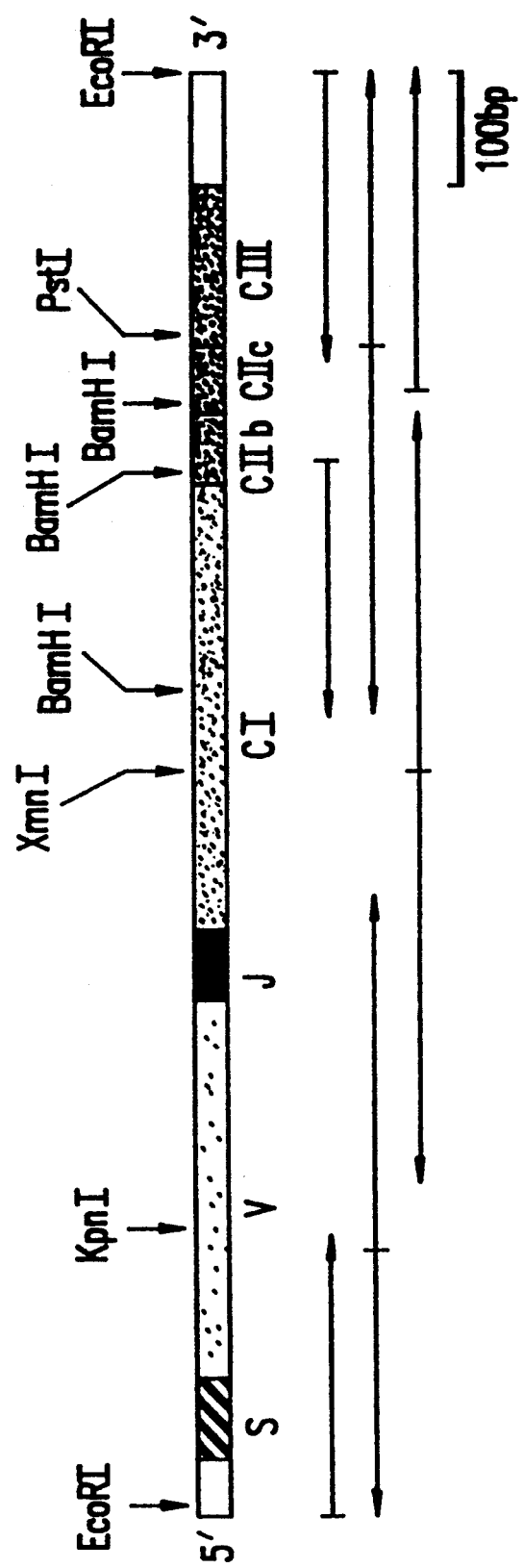

FIGS. 5A-5C. Nucleotide sequence of MOLT-13 δTCR (Form 2bc).

5A) Sequencing strategy of clone M13k. A partial restriction map of the 1.1 kb cDNA clone M13k is shown.

5B,C) Nucleotide and deduced amino acid sequence of clone M13k. Signal sequence (S), variable (V), N-region (N), joining (J) and constant (CI, CIIb, CIIc and CIII) region gene segments are indicated by arrows and were identified by comparison to genomic sequences, described by Lefranc et al., (1986, Cell 45:237-246) (for S and V), Lefranc et al., (1986, Nature, 319:420-422) and Quertermous et al., (1987, Immunol. 138:2687-2690) (for J) and Lefranc et al., (1986, Proc. Natl. Acad. Sci. U.S.A. 83:9596-9600) and Pellicci et al., (1987, Science 237:1051-1055) (for C). The deduced amino acid sequence beginning at the initiator methionine is presented below the nucleotide sequence. Extracellular cysteines are highlighted by boxes, and potential N-linked carbohydrate attachment sites (N-X-S or N-X-T; Marshall, 1977, Ann. Rev. Biochem. 41:673-702) are indicated by brackets.

Figure 6:
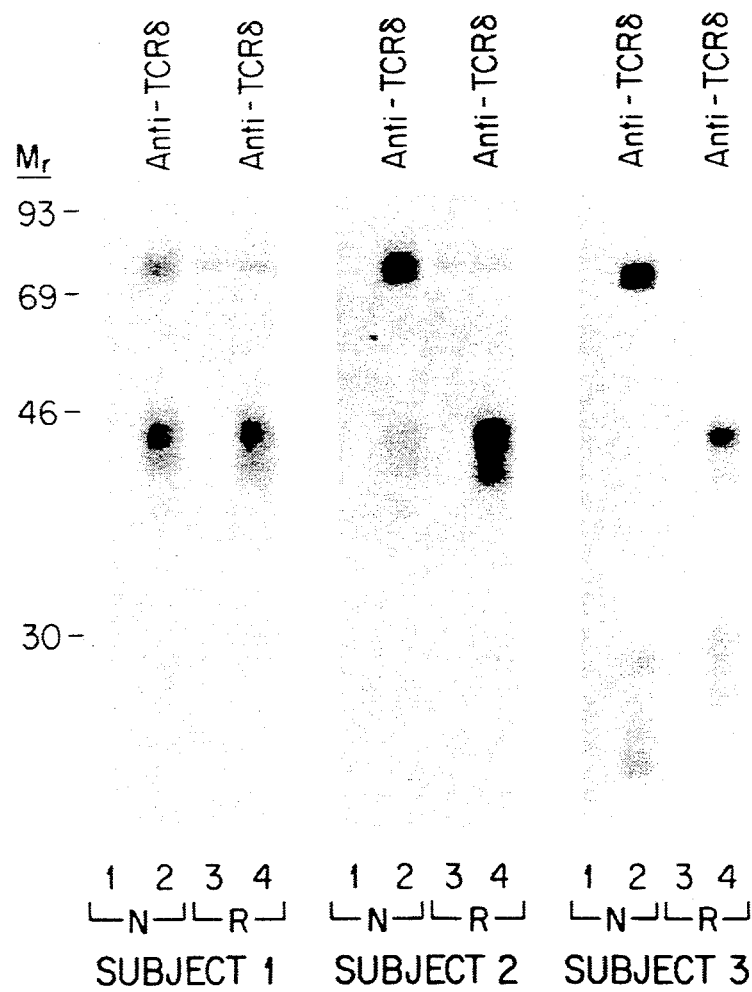

FIG. 6. Preferential use of γ, δTCR Form 1. Freshly isolated peripheral blood mononuclear cells from three healthy donors were $^{125}$I-labelled and solubilized in 1% Triton X-100. Immunoprecipitates with P3 (control, lanes 1 and 3), and anti-TCRδ1 (anti-TCRδ, lanes 2 and 4), were analyzed under nonreducing (N) and reducing (R) conditions. $M_r$ markers in the thousands are shown on the left.

Figure 7:
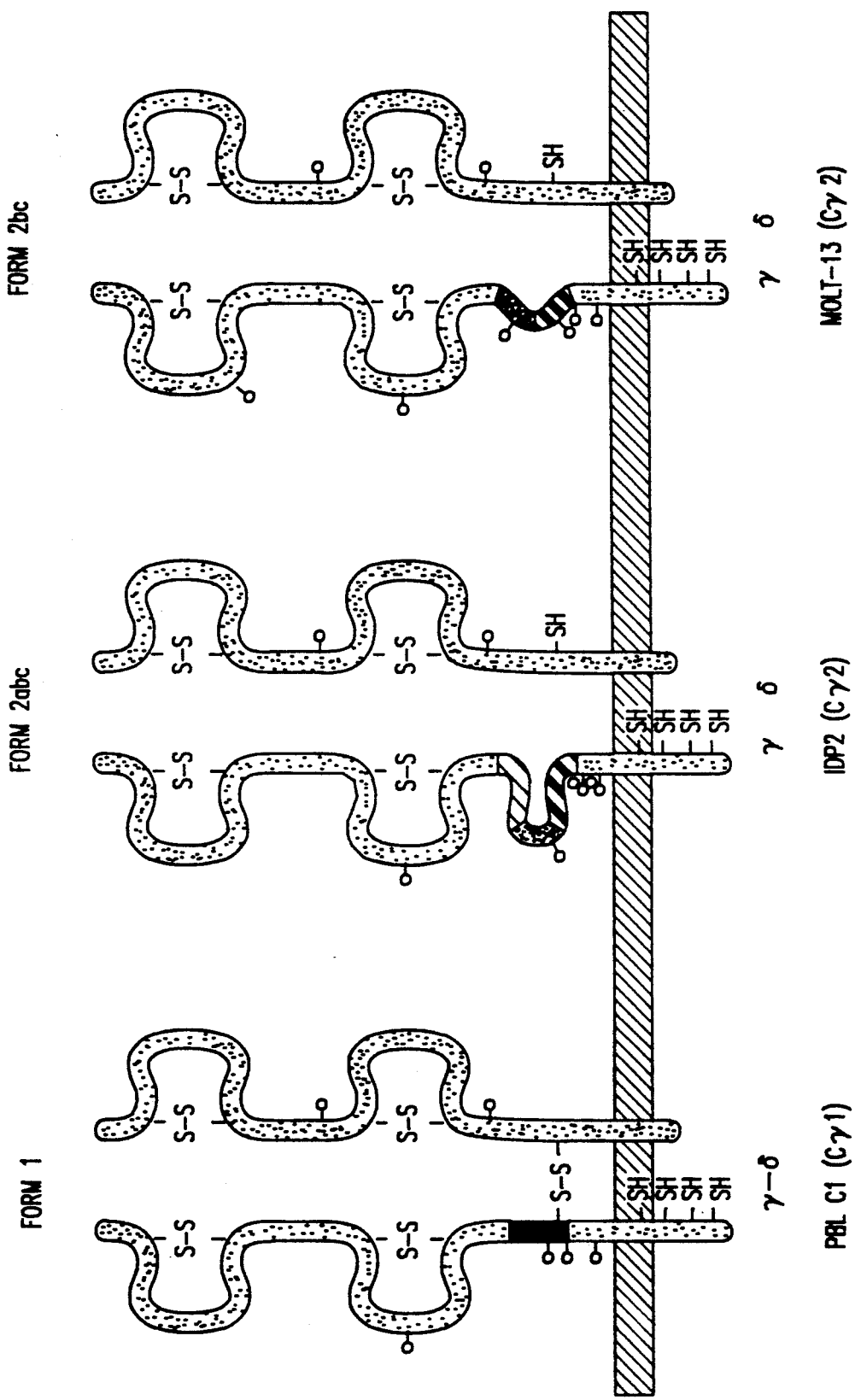

FIG. 7. Schematic representation of the three γ, δTCR forms in man. The CII exon encoded connector peptides are highlighted by filled areas as Cγ1 CII exon encoded peptide as Cγ2 CII exon copy a, copy b, and copy encoded peptides, respectively). Potential N-linked glycan attachment sites (o), and sulfhydryl groups (-SH) and putative disulfide bridges (-S-S-) are indicated.

Figure 8:
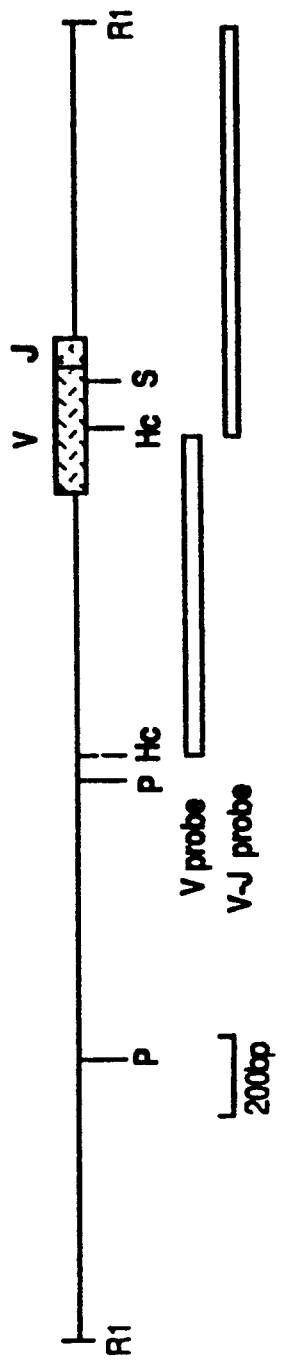

FIG. 8. Map of the rearranged δTCR gene. A map of r 19|δ1 including EcoRI (RI), Hinc II (Hc), ScaI (S) and PvuII (P) sites and probes used in Southern blot analysis is shown.

Figure 9:
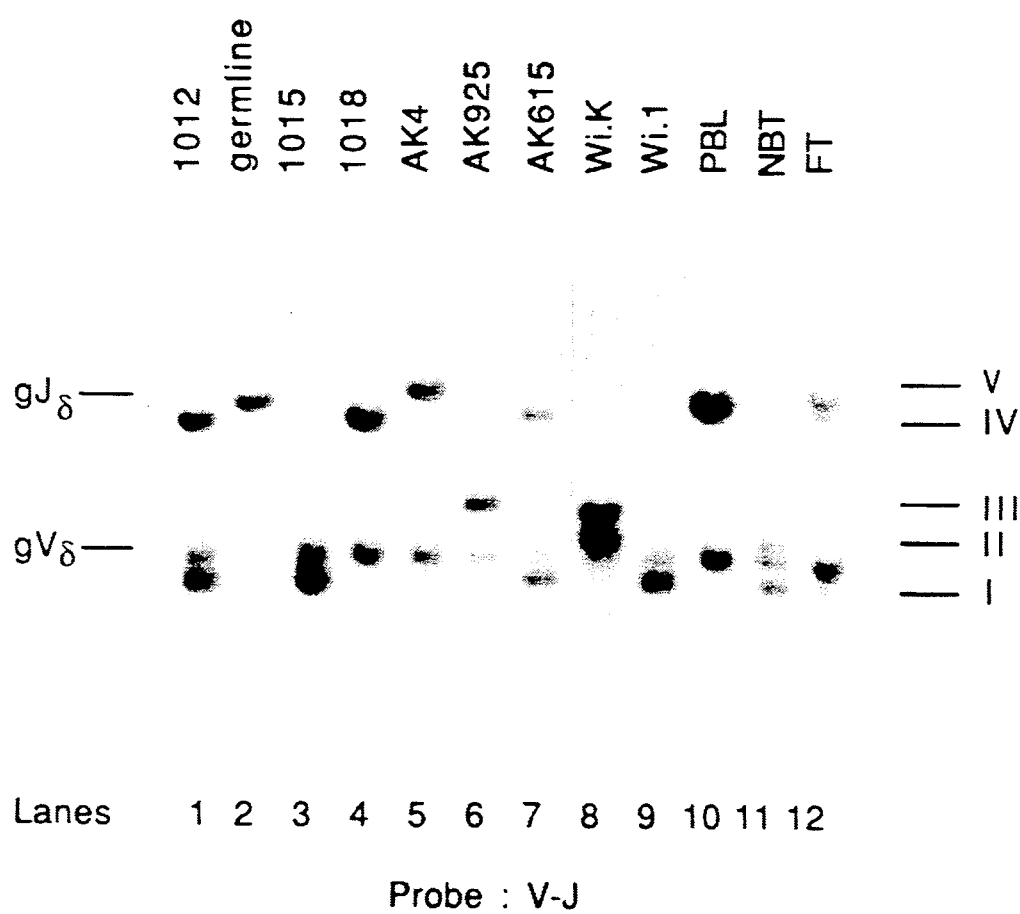

FIG. 9. Southern blot analysis of γ, δ T-cell clones and polyclonal human T-cell populations. Genomic DNA was digested with EcoRI and probed with the V-J probe. DNA sources are: PBL T-cell clones, (lanes 1, 3-9), PBL (lane 10), newborn thymocytes (NBT-lane 11), fetal thymocytes (FT-lane 12), and B cells (germ-line-lane 3.2). The germline 3 kb Vδ and 6.7 kb Jδ fragment are indicated on the left of the blot, while the 5 common rearrangements, numbered I-V are indicated on the right. The sizes of the rearrangements from I-V are 2.9 kb, 3.5 kb, 4.2 kb, 6.2 kb and 7.1 kb respectively.

5. DETAILED DESCRIPTION OF THE INVENTION

5.1. THE δTCR POLYPEPTIDE

The present invention provides a purified polypeptide which comprises at least a portion of a δTCR polypeptide (hereafter referred to as δTCR). This polypeptide may have at least one intrachain, covalent, disulphide bridge. Additionally, the polypeptide may comprise a δTCR polypeptide having a molecular weight of about 40,000 daltons. Furthermore, the δTCR polypeptide may be a human δTCR. In one embodiment of the invention the polypeptide comprises at least a portion of the amino acid sequence shown in FIG. 1.

A substance capable of specifically forming a complex with at least one δTCR polypeptide is also provided by the invention. In one embodiment of the invention, the substance is capable of specifically forming a complex with one δTCR polypeptide. In another embodiment of the invention, the substance is capable of specifically forming a complex with more than one δTCR polypeptide. The substance may be an antibody. In yet another embodiment of the invention, the substance is capable of specifically forming a complex with a variable region of the δTCR polypeptide. The antibody may be a polyclonal antibody or a monoclonal antibody.

Also provided is a method for detecting T cells, each of which has a δTCR polypeptide. This method comprises contacting a sample containing T cells with substances capable of forming complexes with δTCR polypeptides so as to form cellular complexes between the substances and the δTCR polypeptides. These cellular complexes are detected and thereby T cells, each of which has a δTCR polypeptide, are detected.

Accordingly, in one embodiment of the invention, the δTCR polypeptides are present on the surfaces on the T cells. In another embodiment of the invention, the δTCR polypeptides are present in the cytoplasm of the T cells.

This method may be performed by forming complexes with a specific δTCR polypeptide. In one embodiment of the invention, the specific δTCR polypeptide is present only in suppressor T cells.

The invention further provides a method for diagnosing an immune system abnormality in a subject. Within this application, immune system abnormality means a condition of immunological responsiveness to antigens characterized by an increased or a decreased immune response compared to a normal or standard immune response. Accordingly, immune system abnormality includes, but is not limited to, immunodeficiency conditions and diseases, e.g., acquired immune deficiency syndrome and congenital imunodeficiencies and hyperimmune conditions and diseases, e.g., allergies and hayfever. The method of the present invention comprises determining the number of T cells in a sample from the subject and contacting the sample with the substances capable of forming complexes with at least one δTCR polypeptide so as to form cellular complexes between the substances and δTCR polypeptides. The percentage of T cells in the sample which have a δTCR polypeptide is determined and compared with the percentage of T cells which have a δTCR polypeptide in a sample from a normal subject who does not have the immune system abnormality. A difference in the percentage of T cells so determined would be indicative of the immune system abnormality.

In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In still a further embodiment of the invention, the immune system abnormality is an autoimmune disease.

The subject in whom the immune system abnormality is diagnosed may be an animal. In one embodiment of the invention the subject is a human. Furthermore, the sample from the subject may comprise but is not limited to lymphoid tissue, bone marrow, blood, peripheral blood lymphocytes, epithelial cells and the like.

Yet another method for diagnosing an immune system abnormality is provided by the present invention. This method comprises determining the number of δTCR polypeptide bearing T cells in a sample from the subject and the amount of δTCR polypeptide in the δTCR bearing T cells. The amount of δTCR polypeptide so determined is compared with the amount of δTCR polypeptide in an equal number of δTCR polypeptide bearing T cells in a sample from a normal subject who does not have the immune system abnormality. A difference in the amount so determined would be indicative of the immune system abnormality. In one embodiment of the invention, the amount of a single δTCR polypeptide is determined.

A further method for diagnosing an immune system abnormality in a subject is provided. This method comprises: (a) determining in a sample from the subject the ratio of the number of T cells which have a δTCR polypeptide relative to the number of T cells which have a surface marker selected from the group consisting of T4, T8 and $\alpha,\beta$TCR; and (b) comparing the ratio of (a) to the ratio determined in a sample from a subject who does not have the immune system abnormality.

The present invention also provides a nucleic acid molecule encoding a δTCR polypeptide having a molecular weight of about 40,000 daltons. In one embodiment of the invention, the molecule is a DNA molecule. In another embodiment of the invention the DNA molecule comprises at least a portion of the nucleic acid sequence shown in FIG. 1. Further provided is a nucleic acid molecule which is complementary to the nucleic acid molecule which encodes a δTCR polypeptide.

5.2. THE γTCR POLYPEPTIDE

A purified polypeptide which comprises at least a portion of a γTCR polypeptide is also provided by the present invention. In one embodiment of the invention the γTCR polypeptide has a molecular weight of about 40,000 daltons (Form 1). In another embodiment of the invention the γTCR polypeptide has a molecular weight of about 55,000 daltons (Form 2abc). Form 2abc γTCR polypeptide has a slightly larger peptide backbone and contains one extra potential N-linked glycan than Form 1. Form 1 and Form 2abc γTCR polypeptides are more fully described in copending application Serial Nos. 882,100 filed Jul. 3, 1986 and 016,252 filed Feb. 19, 1987, which are incorporated by reference in their entirety. In yet another embodiment of the invention the γTCR polypeptide has a molecular weight of about 40,000 (Form 2bc). Form 2bc γTCR polypeptide possesses a slightly smaller peptide backbone and 2-3 less potential N-linked glycans. Form 2bc γTCR polypeptide may comprise any portion of the primary amino acid sequence of the γTCR polypeptide shown in FIG. 5. Additionally, the γTCR polypeptide may be a human γTCR polypeptide.

The present invention further provides a purified complex which comprises two γTCR polypeptides of the present invention associated with each other. In one embodiment of the invention, the two γTCR polypeptides are associated with each other through at least one interchain, covalent, disulfide linkage. In another embodiment of the invention, the two γTCR polypeptides are noncovalently associated with each other. In still another embodiment of the invention, the two γTCR polypeptides have the same constant domain. In yet a further embodiment of the invention, the two γTCR polypeptides have different constant domains.

The present invention also provides a substance capable of specifically forming a complex with at least one γTCR polypeptide. In one embodiment of the invention, the substance is capable of specifically forming a complex with one γTCR polypeptide. In another embodiment of the invention, the substance is capable of specifically forming a complex with more than one γTCR polypeptide. The substance may be an antibody. In one embodiment of the invention, the antibody is a polyclonal antibody. In another embodiment of the invention, the antibody is a monoclonal antibody.

A method for detecting T cells, each of which has a γTCR polypeptide, is further provided. This method comprises contacting a sample which contains T cells with substances capable of forming complexes with γTCR polpeptides so as to form cellular complexes between the substances and the γTCR polypeptides. These cellular complexes are detected and thereby T cells, each of which has a γTCR polypeptide, are detected.

In one embodiment of the invention, the γTCR polypeptides are present on the surfaces of the T cells. In another embodiment of the invention, the γTCR polypeptides are present in the cytoplasm of the T cells.

In one embodiment of the invention, the substances are capable of forming complexes with a specific γTCR polypeptide. The specific γTCR polypeptide may be present only in suppressor T cells. Furthermore, the γTCR polypeptide may be associated with another γTCR polypeptide. In one embodiment of the invention, the γTCR polypeptide is associated with another γTCR polypeptide only in non-major histocompatibility restricted cytotoxic T lymphocytes. Furthermore, the non-major histocompatibility complex restricted cytotoxic T lymphocytes may be killer T cells or natural killer-like cells.

The present invention further provides a method for diagnosing an immune system abnormality in a subject. This method comprises determining the number of T cells in a sample from the subject and contacting the sample with substances capable of forming complexes with at least one γTCR polypeptide so as to form cellular complexes between the substances and γTCR polypeptides. The percentage of T cells in the sample which have a γTCR polypeptide is determined and compared with the percentage of T cells which have a γTCR polypeptide in a normal subject who does not have the immune system abnormality. A difference in the percentage of T cells so determined would be indicative of the immune system abnormality. In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In still a further embodiment of the invention, the immune system abnormality is an autoimmune disease.

The subject in which the immune system abnormality is diagnosed may be an animal. Additionally, the subject in which the immune system abnormality is diagnosed may be a human. Furthermore, the sample from the subject epithelial cells may comprise but is limited to bone marrow, blood, peripheral blood lymphocytes, and the like.

Another method for diagnosing an immune system abnormality in a subject is provided by the present invention. This method comprises determining the number of γTCR polypeptide bearing T cells in a sample from the subject and the amount of γTCR polypeptides in the γTCR polypeptide bearing T cells. The amount of γTCR polypeptides so determined is compared with the amount of γTCR polypeptides in an equal number of γTCR polypeptide bearing T cells in a sample from a normal subject who does not have the immune system abnormality. A difference in the amount so determined would be indicative of the immune system abnormality. In one embodiment of the invention, the amount of a single γTCR polypeptide is determined.

Yet another method is provided for diagnosing an immune system abnormality in a subject. This method comprises: (a) determining in a sample from the subject the ratio of the number of T cells which have a Form γTCR polypeptide relative to the number of T cells which have a surface marker selected from the group consisting of Form 2abc γTCR, Form 2bc γTCR, T4, T8, and α/βTCR; and (b) comparing the ratio of (a) to the ratio determined in a sample from a subject who does not have the immune system abnormality, where a difference in the ratios so determined is indicative of the immune system abnormality.

Provided is a further method for diagnosing an immune system abnormality in a subject. This method comprises: (a) determining in a sample from the subject the ratio of the number of T cells which have a Form 2abc γTCR polypeptide relative to the number of T cells which have a surface marker selected from the group consisting of Form 1 γTCR, Form 2bc γTCR T4, T8, and α/βTCR; and (b) comparing the ratio of (a) to the ratio determined in a sample from a subject who does not have the immune system abnormality, where a difference in the ratios so determined is indicative of the immune system abnormality.

Another method for diagnosing an immune system abnormality in a subject is provided. This method comprises: (a) determining in a sample from the subject the ratio of the number of T cells which have a Form 2bc γTCR polypeptide relative to the number of T cells which have a surface marker selected from the group consisting of Form 1 γTCR, form 2abc γTCR, T4, T8, and α,βTCR; and (b) comparing the ratio of (a) to the ratio determined in a sample from a subject who does not have the immune system abnormality.

The present invention also provides a nucleic acid molecule encoding a γTCR polypeptide having a molecular weight of about 40,000 daltons (Form 2bc). The constant region of Form 2bc γTCR polypeptide is encoded by the cγ2 gene segment containing three cII exons. Only two of the three cII exons are utilized. The molecule is a DNA molecule in one embodiment of the invention. In another embodiment of the invention the DNA molecule comprises at least a portion of the nucleic acid sequence shown in FIG. 5.

5.3. THE γδ POLYPEPTIDE COMPLEX

A purified complex which comprises at least a portion of a δTCR polypeptide and at least a portion of a γTCR polypeptide is further provided by the present invention. This complex may comprise a δTCR polypeptide having a molcular weight of about 40,000 daltons and a γTCR polypeptide having a molecular weight of about 40,000 daltons (Form 1 and Form 2bc) or 55,000 daltons (Form 2abc). Furthermore, the δTCR polypeptide may be a human δTCR polypeptide, and the γTCR polypeptide may be a human γTCR polypeptide. Moreover, the δTCR polypeptide and the Form 1 γTCR polypeptide may be associated with each other through at least one interchain, covalent, disulphide linkage. In another embodiment, the δT cell receptor polypeptide and the Form 2abc or Form 2bc γTCR polypeptide may be noncovalently associated with each other. Also provided is a substance capable of specifically forming a complex with at least one γ, δTCR complex. This substance may be capable of forming a complex with one γ, δTCR complex. Furthermore, the substance may be capable of forming a complex with more than one γ, δTCR complex.

In one embodiment of the invention, the substance is an antibody. In another embodiment of the invention, the substance is a polyclonal antibody. In yet another embodiment of the invention, the substance is a monoclonal antibody.

The present invention further provides a method for detecting T cells, each of which has a γ, δTCR complex. This method comprises contacting a sample containing T cells with substances capable of forming complexes with γ, δTCR complexes so as to form and subsequently detect cellular complexes between the substances and the γ, δTCR complex. In one embodiment of the invention, the γ, δTCR complexes are present on the surface of the T cells. In another embodiment of the invention, the γ, δTCR complexes are present in the cytoplasm of the T cells. In yet another embodiment of the invention, the substances are capable of forming complexes with a specific γ, δTCR complex. The specific γ, δTCR complex may be present only in suppressor T cells.

A method for diagnosing an immune system abnormality in a subject is further provided by the present invention. This method comprises determining the number of T cells in a sample from the subject and contacting the sample with substances capable of forming complexes with at least one γ, δTCR complex so as to form cellular complexes between the substances and γ, δTCR complexes. The percentage of T cells in the sample which have a γ, δTCR complex is determined and compared with the percentage of T cells which have a γ, δTCR complex in a sample from a normal subject who does not have the immune system abnormality. A difference in the percentage of T cells so determined would be indicative of the immune system abnormality. In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In yet a further embodiment of the invention, the immune system abnormality is an autoimmune disease.

The subject in which the immune system abnormality is diagnosed may be an animal. Furthermore, the subject in which the immune system abnormality is diagnosed may be a human. Moreover, the sample from the subject may comprise but is not limited to bone marrow, blood, peripheral blood lymphocytes, epithelial cells and the like.

Still another method for diagnosing an immune system abnormality in a subject is provided by the present invention. This method comprises determining the number of γ, δTCR complex bearing T cells in a sample from the subject and the amount of γ, δTCR complexes in the γ, δTCR complex bearing T cells. The amount so determined is compared with the amount of γ, δTCR complexes in an equal number of γ, δTCR complexes bearing T cells in a sample from a normal subject who does not have immune system abnormality. A difference in the amount so determined would be indicative of the immune system abnormality. In one embodiment of the invention, the amount of a single γ, δTCR complex is determined.

The present invention provides yet another method for diagnosing an immune system abnormality in a subject. This method comprises: (a) determining in a sample from the subject the ratio of the number of T cells which have a γ (Form 1), δTCR complex relative to the number of T cells which have a surface marker selected from the group consisting of Form 2abc γTCR, Form 2bc γTCR, T4, T8, and α/βTCR; and (b) comparing the ratio of (a) to the ratio determined in a sample from a subject who does not have the immune system abnormality, where a difference in the ratios so determined is indicative of the immune system abnormality.

A further method for diagnosing an immune system abnormality in a subject is provided. This method comprises: (a) determining in a sample from the subject the ratio of the number of T cells which have a γ (Form 2abc), δTCR complex relative to the number of T cells which have a surface marker selected from the group consisting of Form 1 γTCR, Form 2bc γTCR, T4, T8, and α/βTCR; and (b) comparing the ratio of (a) to the ratio determined in a sample from a subject who does not have the immune system abnormality, where a difference in the ratios so determined is indicative of the immune system abnormality.

Yet another method is provided for diagnosing an immune system abnormality in a subject. This method comprises: (a) determining in a sample from the subject the ratio of the number of T cells which have a γ (Form 2bc), δTCR complex relative to the number of T cells which have a surface marker selected from the group consisting of Form 1γTCR, Form 2abc γTCR, T4, T8, and α/βTCR; and (b) comparing the ratio of (a) to the ratio determined in a sample from a subject who does not have the immune system abnormality, where a difference in the ratios so determined is indicative of the immune system abnormality, where a difference in the ratios so determined is indicative of the immune system abnormality.

The various methods for diagnosing abnormalities and for detecting T cells provided by the present invention are based upon the novel polypeptides and substances capable of forming complexes with these polypeptides as described more fully herein above. The methods utilize methods for detecting and quantifying T cells, including but not limited to, fluorescence activated cell sorting and autoradiography, which are well known to those skilled in the art to which this invention pertains.

6. EXAMPLE: THREE FORMS OF THE HUMAN T CELL RECEPTOR γδ: PREFERENTIAL USE OF ONE FORM IN SELECTED HEALTHY INDIVIDUALS

6.1. EXPERIMENTAL PROCEDURES 6.1.1. ANTIBODIES

Monoclonal antibodies used were anti-Leu4 (anti-CD3) (Ledbetter et al., 1981, J. Exp. Med. 153:310-323), βF1 (anti-βTCR) (Brenner et al., 1987, J. Immunol. 138:1502-1509), anti-TCRδ1 (anti-δTCR) (described more fully in copending U.S. application Ser. No. 115,256 filed Oct. 29, 1987, now U.S. Pat. no. 5,024,940, issued Jun. 18, 1991 which is incorporated in its entirety), P3 (control) (secreted by P3X63. Ag8; Koehler and Milstein, 1975, Nature 256:495-497), 187.1 (rat anti-mouse k light chain) (Yelton et al., 1981, Hybridoma 1:5-11), and WT31 (stains αβTCR lymphocytes brightly) (Spits et al., 1985, J. Immunol 135:1922-1928). Anti-Cγb peptide serum (anti-TCR γ)was generated against a 22 amino acid synthetic peptide (Gln-Leu-Asp-Ala-Asp-Val-Ser-Pro-Lys-Pro-Thr-Ile-Phe-Leu-Pro -Ser-Ile-Ala-Glu-Thr-Lys-Cys) (described more fully in copending U.S. application Ser. No. 882,100 filed Jul. 3, 1986 and U.S. Pat. No. 5,024,940, issued Jun. 17, 1991, which is incorporated in its entirety).

6.1.2. CELL LINES

PEER (Weiss et al., 1986, Proc. Natl. Acad. Sci. U.S.A. 83:6998-7002) and MOLT-13 (isolated by J. Minowada, Loh et al , 1987, Nature 330:569-572) are T leukemic cell lines. Umbilical cord blood derived clone WM-14 (Alarcon et al., 1987, Proc. Natl. Acad. Sci. U.S.A. 84:3861-3865) and peripheral blood derived cell line IDP2 (described more fully in copending U.S. application Ser. No. 882,100 filed Jul. 3, 1986, which is incorporated by reference in its entirety) and thymus-derived Clone II (Bank et al., 1986, Nature 322:179-181) were cultured as described earlier. Peripheral blood derived cell line 2 (PBL-L2) was isolated by sorting peripheral blood isolated lymphocytes that did not stain with mAb WT31. The isolated cells were then expanded in vitro in RPMI 1640 medium supplemented with 10% (v/v) conditioned medium containing IL-2 and 10% (v/v) human serum, and stimulated every 3 weeks with irradiated autologous feeder cells.

6.1.3. IODINATION AND IMMUNOPRECIPITATION $2 \times 10^7$ cells were isolated by Ficoll-diatrizoate (Organon Teknika Corp.) centrifugation and iodinated on ice in 0.5 ml of phosphate-buffered saline, pH 7.4 (PBS) containing 1 mM $MgCl_2$, 5 mM glucose by adding 100 μg of lactoperoxidase (80-100 U/mg, Sigma) and 1 mCi of $Na^{125}I$ (New England Nuclear). Ten μl of a 0.03% hydrogen peroxide solution was added at 5 minute intervals over a reaction period of 30 minutes. Cells were solubilized overnight in detergent supplemented TBS (50 mM Tris-Base pH 7.6, 140 mM NaCl) containing 1 mM phenylmethylsulfonyl fluoride (PMSF, Sigma) and 8 mM iodoacetamide (IAA, Sigma). As indicated, different detergents used in this study were 0.3% (w/v) 3-[(3-cholamidopropyl) dimethylammonio] 1-propanesulfonate (CHAPS, Signma), 1% (w/v) digitonin (Aldrich) and Triton X-100 (TX-100, Sigma). After 20 minutes of centrifugation at 10,000 g to remove insoluble material, detergent lysates were precleared by a 30 minute incubation with 4 μl of normal rabbit serum (NRS) and 400 μl of 187.1 hybridoma culture medium, followed by addition of 200 μl of a 10% (w/v) cell suspension of fixed Staphylococcus aureus Cowan I (Pansorbin, Calbiochem). After a one-hour incubation, Pansorbin was removed by centrifugation. Specific precipitations were carried out by adding 0.25 μl βF1 ascites, 1 μl mg/ml anti-Leu4 or 0.25 μl P3 ascites, together with 150 μl of 187.1 culture supernatant to each sample, followed by a one-hour incubation. 100 μl of 10% (v/v) Protein A-Sepharose (Pharmacia) was added and the mixture was rocked for 1 hour at 4° C. Immunoprecipitates were washed five times with 0.1% (v/v) Triton X-100 containing TBS and analyzed by SDS-PAGE (Laemmli, 1970, Nature 227:680–685).

For immunoprecipiations with the anti-Cγb peptide serum, iodinated cells were solubilized in 1% (w/v) sodium dodecyl sulfate (SDS) containing TBS and then boiled for 3 minutes. After cooling, 5 volumes of 2% (v/v) Triton X-100 in TBS containing PMSF and IAA was added, together with 200 μl of a mixture of 1 mg/ml DNAse and 0.5 mg/ml RNAse in 50 mM $MgCl_2$. Preclearing and immunoprecipitations were performed as described above, omitting the addition of 187.1 mAb. Immunoprecipitates were washed in TBS containing 0.5% (v/v) TritonX-100, 0.5% (w/v) deoxycholate (DOC), 0.05% (w/v) SDS.

6.1.4. BIOSYNTHETIC LABELLING $4 \times 10^7$ exponentially growing cells were resuspended in 4 ml of methionine and cysteine-free RPMI 1640 (Select-Amine kit, Gibco) supplemented with 10% dialyzed FCS and 20 mM Hepes. After a 30 minute starvation period at 37° C., 1 mCi of $^{35}$S-methionine and 1 mCi of $^{35}$S-cysteine were added, allowing a 15 minute labelling period. Cells were harvested and solubilized in 2% (v/v) Triton X-100, TBS. Preclearing and immunoprecipitations were performed as described above. The immunoprecipitates were washed four times in 0.5% (v/v) Triton X-100, 0.5% (w/v) deoxycholic acid, 0.05% (w/v) SDS, TBS followed by three washes in 0.5% (v/v) Triton X-100, 0.5 M NaCl, 5 mM EDTA, 50 mM Tris, pH 7.6. The samples were analyzed by SDS-PAGE and visualized by standard fluorography procedures (Bonner and Laskey, 1974, Eur. J. Biochem. 46:83–88).

6.1.5. GEL PURIFICATION OF δTCR PROTEINS

Surface iodinated cells were solubilized in 0.3% (w/v) CHAPS-TBS and immunoprociptated using 50 μl of anti-Leu4-coupled Sepharose beads. The immunoprecipitated species were resolved by SDS-PAGE under nonreducing conditions and the wet gel was exposed for 24 hours at 4° C. on XAR-5 film (Kodak) to visualize radiolabelled δTCR proteins. The gel regions corresponding to δTCR were excised, incubated in 5% (v/v) 2-mercaptoethanol containing sample buffer and resolved a second time by SDS-PAGE. Because of the characteristic SDS-PAGE mobility shift upon reduction, δTCR protein could be separated and then purified from contaminants. TCR proteins were eluted from gel slices by overnight incubation in 0.05% (w/v) SDS, 50 mM ammonium bicarbonate buffer at 37° C. and lyophilized.

6.1.6. ENDOGLYCOSIDASE DIGESTION

For endoglycosidase H (Endo H) digestions, immunoprecipitated material or gel purified protein was boiled for 3 minutes in a 40 μl % (w/v) SDS solution containing 0.14 M 2-mercaptoethanol. After cooling, the mixture was diluted with 360 μl of 0.15 M acetate buffer, pH 5.5 containing 1 mM PMSF. Five μl Endo H (1U/ml- Endo-β-N-acetylglucosaminidase H, Genzyme) was incubated with half of the above solution for 14 hours at 37° C., while the other half was mock treated.

For N-glycanase (N-GLY) digestion, gel purified material was boiled for 3 minutes in 35 μl of 0.5% (w/v) SDS, 0.10 M 2-mercaptoethanol. Then, 100 μl of 0.2 M sodium phosphate (pH 8.6), 1.25% (v/v) Triton X-100 was added. Half of the mixture was incubated with 1 μl N-Glycanase (250 U/ml, peptide-N-[N-acetyl-β-glucosaminyl]asparagine amidase; Genzyme) and incubated for 16 hours at 37° C., while the other half was mock treated.

After digestion 10 μg bovine serum albumin was added as carrier and samples were recovered by trichloroacetic acid precipitation. Protein pellets were taken up in sample buffer containing 5% (v/v) 2-mercaptoethanol.

6.1.7. PRODUCTION OF MONOCLONAL ANTIBODY anti-Cγml

Part of the Cγ CI and CII exons of HPB-MLT pTγ-1 was isolated using the BamHI and PstI sites at nucleotide positions 571 and 848 (Dialynas et al., 1986, Proc. Natl. Acad. Sci. USA 83:2619–2623) and was cloned into expression vector pRIT2T (Pharmacia). The resulting Protein A fusion protein was expressed in E. coli N4830. Bacteria were lysed with lysozyme and the fusion protein was isolated by purification over a IgG Sepharose column. Mice were injected intraperitoneally with 100 μg of fusion protein in Freund's adjuvant at days 0, 7 and 28. Twenty-eight days later 100 μg of fusion protein in PBS was injected intravenously. After three days splenocytes were isolated and fused with the hybridoma P3X63Ag8.653 as described (Brenner et al., 1987, J. Immunol. 138:1502–1509). Hybridomas were screened by enzyme-linked immunoabsorbent assay (ELISA). Ninety six-well flat bottom plates (LINBRO, Flow Laboratories) were incubated overnight with 0.4 μg of fusion protein or nonfused protein in PBS. Nonspecific binding sites were blocked at 23° C. with 0.25 mg/ml normal rabbit IgG (Sigma) in PBS containing 50% (v/v) FCS. 50 μl of hybridoma supernatant was added for 1 hour at 4° C., followed by a similar incubation in 50 μl of a 5 μg/ml solution of peroxidase-conjugated anti-mouse IgG (Cappel). All described incubations were interspersed with washing steps, using 10% (v/v) FCS, 0.1% (w/v) BSA, PBS. The ELISA was developed with 0.08% (w/v) O-phenylene diamine (Sigma) in 0.012% (w/v) hydrogen peroxide containing phosphatecitrate buffer, pH 5.0.

Although anti-Cγml (IgG$_1$) does not recognize the native γδTCR/CD3 complex in cytofluorographic analysis nor the γδTCR heterodimer from TX-100 solubilized cells in immunoprecipitation (data not shown), it does recognize biosynthetically labelled γTCR precursor and mature γTCR proteins after separation of CD3/γδTCR proteins into individual chains. In this way, anti-Cγml was shown to recognize the γTCR protein after separating CDγδTCR complexes into individual chains by boiling anti-CD3 immunoprecipitates in 1% (w/v) SDS in TBS (FIG. 3, lane 3).

6.1.8. ISOLATION AND SEQUENCING OF A MOLT-13 γTCR cDNA CLONE

Poly (A)+ RNA was prepared from MOLT-13 cells by urea/lithium chloride precipitation followed by oligo (dT) cellulose affinity chromatography. A λgt 10 cDNA library was prepared from poly(A)+ RNA by the method of Huynh et al., 1985 (DNA Cloning, Glover, D.M. ed. IRL Press, Oxford, I:49-78) using Mung Bean Nuclease for the hairpin loop cleavage (McCutcham et al., 1984, Science 225:626-628). The cDNA library was amplified on the E. coli strain C600 Hf and screened by plaque filter hybridization with $^{32}$P-labelled PTγI (Dialynas et al., 1986, Proc. Natl. Acad. Sci. U.S.A. 83:2619-2623). Positive clones were analyzed for size and restriction enzyme map, and cDNA clone M13k was selected for sequencing. The cDNA of M13k was excised from λgt 10 phage with the endonuclease EcoRI and further digested with appropriate restriction enzymes. The fragments were subcloned into M13 vectors and sequenced by the dideoxy chain termination method (Sanger et al., 1977, proc. Natl. Acad. Sci. U.S.A. 74:5463-5467) using the modified T7 polymerase (Sequenase, United States Biochemical Corp.).

Clone M13k corresponds to a full length, in frame, γTCR transcript, including 36 nucleotides of 5' untranslated region and 72 nucleotides of 3' noncoding region (FIG. 5). The nucleotide sequence of the V region is identical to the genomic Vγ1.3 sequence (nomenclature Lefranc et al., 1986a, Cell 45:237-246; Strauss et al., 1987, Science 237:1217-1219), except for a C to T (Ile to Val) change of nucleotide 53 in the putative signal sequence. The J region is identical to the Jγ2.3 sequence (nomenclature based on Lefranc et al, 1986b, Nature 319:420-422; Quertermous et al, 1987, J. Immunol. 138:2687-2690). Interestingly, 8 nucleotides occur at the V-J junction which do not appear to be encoded by the genomic V or J sequences and presumably represents an N-region. The C region sequences match the corresponding genomic sequence (Lefranc et al., 1986c, Proc. Natl. Acad. Sci. U.S.A. 83:9596-9600), with the exception of nucleotide 559 (G to C; Val to Ile) and nucleotide 908 (T to C; Met to Thr).

6.2. RESULTS

6.2.1. NOVEL γδTCR PROTEIN COMPLEX

Preliminary studies of peripheral blood γδTCR lymphocytes revealed the presence of a CD3-associated complex that was different from the known human γδTCR forms. In an attempt to delineate this form, we produced and characterized a number of cell lines derived from normal human donors. Peripheral blood lymphocytes were stained with monoclonal antibody (mAb) WT31, which brightly stains resting αβTCR lymphocytes. Cells that did not stain were isolated by cell sorting and then expanded in vitro in IL-2 containing medium. Peripheral blood lymphocyte line 2 (PBL-L2) obtained in this way, proved to be homogeneously CD3+CD4−CD8−, a cell surface phenotype characteristic of γδTCR lymphocytes.

To visualize γδTCR complexes on PBL-L2 cells, immunoprecipitations with an anti-CD3 mAb were carried out from cell surface $^{125}$I-labelled cells solubilized in CHAPS or digitonin. In these detergents, the physical association between the CD3 complex and γδTCR subunits is preserved. SDS-PAGE of anti-CD3 immunoprecipitates from PBL-L2 cells resolved 40kD and 44kD proteins (referred to as 40kD) that were identified as γTCR subunits by anti-Cγb serum, an antiserum directed against a γTCR constant region peptide (FIG. 2A; see methods section).

These γTCR proteins on PBL-L2 are noncovalently associated with a δTCR subunit, which is visible as a weakly iodinated protein in the anti-CD3 immunoprecipitation analyzed under nonreducing conditions (FIG. 2A, lane 6, closed arrow). This weakly iodinated protein represents the δTCR subunit on PBL-L2 cells, since it is not recognized by anti-Cγb serum (FIG. 2A, lane 8). In addition, it displays the same SDS-mobility shift comparing analysis under nonreducing and reducing conditions as was noted for the δTCR proteins on IDP2 and PEER cells (see infra; described more fully in copending U.S. application Ser. No. 016,252 filed Feb. 19, 1987 which is incorporated by reference in its entirety). The δTCR protein could not be visualized after reduction (FIG. 2A, lane 3), because it migrated with a mobility of 40kD (see infra) and then was obscured by the similar sized γTCR protein (open arrow).

Figure 2E:
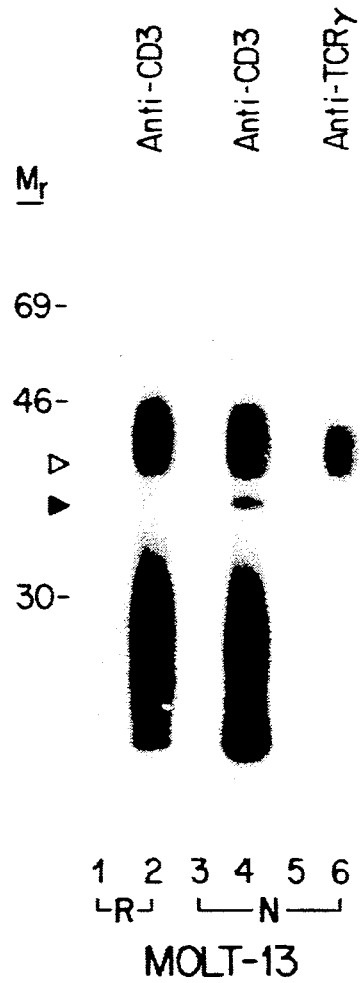

This γδTCR form is not only present on normal peripheral blood T-lymphocytes, but is also observed on thymus-derived Clone II cells (FIG. 2D, Bank et al., 1986, Nature 322:179-181), and on the T-leukemic cell line MOLT-13 (FIG. 2E). These three cell lines possess γTCR species that display differential glycosylation resulting in a γTCR protein doublet observed on PBL-L2 (40kD and 44kD; FIG. 2A, lane 8) and Clone II cells (40k D and 44kD; FIG. 2D, lane 8) or a diffusely labelled γTCR protein band observed on MOLT-13 cells (40 to 46kD; FIG. 2E, lane 6). Two-dimensional gel analysis [noneqiilibrium pH gradient electrophoresis (NEPHGE) followed by SDS-PAGE] of the MOLT-13 γTCR protein band resolved two parallel γTCR species (40kD and 44kD), of which the 44kD γTCR species contained an additional high mannose (or hybrid) N-linked glycan compared to the 40kD γTCR species (data not shown). Thus, the γTCR subunits of this receptor complex isolated from three different cell sources (peripheral blood, thymus, and leukemia) reveal cell surface species of 40kD that are noncovalently associated with δTCR partner chains.

For comparison to the γδTCR form on PBL-L2, Clone II and MOLT-13 cells, we examined the previously known forms on the IDP2 and WM-14 cell lines. The IDP2 cell line (described more fully in copending U.S. application Ser. No. 882,100 filed Jul. 3, 1986, which is incorporated by reference in its entirety) contains a larger, 55-60kD γTCR protein (referred to as 55kD), which is recognized by anti-Cγb serum (FIG. 2B). When the anti-CD3 immunoprecipitate is examined under nonreducing conditions, it is evident that the IDP2 γTCR protein is associated noncovalently with its δTCR partner chain (FIG. 2B, lane 4, solid arrow). Upon reduction, the δTCR protein displays a decrease in SDS-PAGE mobility to a relative molecular mass of 40kD (compare FIG. 2B, lane 4, closed arrow, with FIG. 2B, lane 2, open arrow).

In contrast to the noncovalently associated γδTCR forms, the peripheral blood-derived T cell clone, WM-14, bears a disulfide-linked TCR dimer of 70kD (FIG. 2C, lane 7), that was recognized by anti-Cγserum (Alarcon et al, 1987, Proc. Natl. Acad. Sci. U.S.A. 84:3861-3865). This dimer is also recognized by anti- TCRδ1, a mAb directed against the δTCR subunit (FIG. 2C, lane 5), and therefore represents a γδTCR heterodimer. Analysis under reducing conditions reveals three γTCR proteins of 36kD, 40kD and 43kD (referred to as 40kD). The molecular mass of the δTCR subunit in this complex is not known.

Thus, the CD3-associated complex on PBL-L2, Clone II and MOLT-13 cells constitutes a novel γδTCR heterodimer compared to the previously known forms, since its TCR γ subunit is 40kD (similar in size to the disulfide-linked Cγ1 encoded γTCR protein on WM-14 cells), yet it is not disulfide-linked to its partner chain (similar to the 55kD, Cγ2 encoded γTCR protein on IDP2 cells). To understand the molecular basis of this complex more detailed structural analysis of its γTCR and δTCR subunits was carried out, using the MOLT-13 cell line as an example.

6.2.2. CORE POLYPEPTIDE SIZE OF MOLT-13 γTCR SUBUNIT

To determine the size of the γTCR core polypeptide of MOLT-13 cells (40kD γTCR glycoprotein), and compare it with that of PEER cells (55kD γTCR glycoprotein), both cell lines were biosynthetically labelled for 15 minutes in the presence of $^{35}$S-methionine and $^{35}$S-cysteine, solubilized in Triton X-100 and then immunoprecipitated with anti-Cγml, a new monoclonal antibody that specifically recognizes the γTCR chain (FIG. 4A, see methods section). Immunoprecipitated material was subsequently digested with endoglycosidase H (Endo H) to remove the immature N-linked glycans. The MOLT-13 γTCR polypeptide backbone has a relative molecular mass of 35 kD (FIG. 4A, lane 8), which is 5kD smaller than the PEER γTCR core polypeptide (40kD; FIG. 4A, lane 4) or the IDP2 γTCR core polypeptide (40kD; described more fully in copending U.S. application Ser. No. 016,252, filed Feb. 19, 1987, which is incorporated by reference in its entirety). It now can be concluded that MOLT-13 cells express a γTCR core polypeptide that is distinct from the IDP2 and PEER γTCR core polypeptides based on its being 5kD smaller. In addition, only 5–11kD of size on the mature MOLT-13 γTCR cell surface glycoprotein are accounted for by post-translational processes (40–46kD surface size minus 35kD core size), where 15–20kD of relative molecular mass can be accounted for by post-translational processes on the PEER and IDP2 γTCR glycoproteins (55–60kD surface size minus 40kD core size). Assuming that all post-translational processes are N-linked glycans and that each glycan chain accounts for approximately 3kD of relative molecular mass, we predict that 2 to 3 N-linked glycans are attached to the MOLT-13 γTCR protein, while 5 N-linked glycans are added to the polypeptides on PEER and IDP2 cells. Experiments using N-glycanase to remove N-linked carbohydrates from cell surface γTCR proteins showed that the majority of the post-translational processes that are added to the core polypeptide are indeed N-linked glycans (data not shown).

6.2.3. PRIMARY SEQUENCE OF MOLT-13 γTCR

To understand the structure of the constant region gene segment encoding the MOLT-13 γTCR subunit, the sequence of a cDNA clone representing the MOLT-13 γTCR transcript was determined. A λgt10 library from MOLT-13 derived poly-A+ RNA was constructed and probed with a human γTCR cDNA clone, pTγ-1 (Dialynas et al., 1986, supra). Based on size and limited restriction enzyme mapping one clone, M13k, was selected and its nucleotide sequence determined (FIG. 5). Clone M13k represents a full length, in-frame γTCR transcript, using a Vγ1.3 gene segment joined to a Jγ2.3 gene segment (Lefranc et al., 1986a, supra.; Lefranc et al., 1986b, supra.; nomenclature based on Strauss et al., 1987, supra; Quertermous et al., 1987, J. Immunol. 138:2687–2690). The constant region sequence was found to be nearly identical to a recently reported non-functional γTCR (Pellici et al., 1987, Science 287:1051–1055) and to the Cγ2 qenomio sequence containing two CII exon copies b and c (Lefranc et al., 1986c, supra) (see methods section for detailed account). This represents the first in-frame transcript encoding a γTCR protein expressed on the cell surface that utilizes a Cγ2 gene segment with two CII exon copies.

The deduced amino acid sequence of this cDNA clone predicts a polypeptide backbone size of 34.8kD which is in good agreement with biochemical data described above. Surprisingly, six potential N-linked carbohydrate attachment sites are encoded by this transcript. Since the biochemical data suggest that only 2 to 3 N-linked glycans are attached to the polypeptide chain, it indicates that not all potential sites are used.

To reflect Cγ gene segment usage, we have denoted the disulfide-linked γδTCR form expressed by PBL-C1 and WM-14 as "Form 1", since such disulfide-linked γTCR chains utilize the Cγ1 gene segment (Krangel et al., 1987, Science 237, 64–67). The large (55kD), nondisulfide-linked γTCR subunit of the γδTCR form expressed on IDP2 and PEER cells is encoded by Cγ2 gene segments containing three CII exon copies, namely copy a, copy b and copy c (Krangel et al., supra; Littman et al., 1987, Nature 326:85–88) and therefore this γδTCR form is called "Form 2abc" In concordance, the form characterized on MOLT-13 cells is referred to as "Form 2bc"

6.2.4. PREFERENTIAL Cγ GENE SEGMENT USAGE

To determine the presence of these three γ, δTCR forms in freshly isolated peripheral blood we analyzed the mononuclear cells from ten healthy subjects, using biochemical analysis with mAb anti-TCRδ1. This reagent reacts with the great majority, if not all γ, δTCR lymphocytes (described more fully in copending U.S. application Ser. No. 115,256, filed Oct. 29, 1987 now U.S. Pat. No. 5,024,940, issued Jun. 18, 1991 which is incorporated by reference in its entirety). Representative results from this panel are shown in FIG. 6. In subject 1, anti-TCRδ1 immunoprecipitates (analyzed under nonreducing conditions) demonstrate the presence of both disulfide-linked γ, δTCR complexes as a 70kD protein band (Form 1) and nondisulfide-linked γ, δTCR complexes as a broad 40kD protein band (Form 2bc) (FIG. 6, lane 2). This indicates that the Cγ1 and Cγ2 constant regions are both used by the expressed γ, δTCR of this individual. However, the amount of Form 2bc varied among individuals. Note the smaller fraction of Form 2bc in subject 2 compared to subject 1 by comparing the intensity of the 40kD protein bands in both individuals (compare lane 2 of subject 2 with lane 2 of subject 1). Even more strikingly, only disulfide-linked γ, δTCR complexes could be detected on the mononuclear cells of three of the ten individuals examined, even after long exposure of the autoradiographs (see subject 3). None of the analyzed individuals revealed the 55kD, nondisulfide-linked γ, δTCR complex (Form 2abc) in peripheral blood.

6.2.5. CHARACTERIZATION OF THE δTCR SUBUNIT

In contrast to the striking structural differences in size and glycosylation of the γTCR proteins, δTCR subunits from different cell sources proved to be markedly similar. The relative molecular mass of the δTCR glycoprotein on MOLT-13 cells was directly determined to be 40kD using the anti-δTCR mAb (FIG. 3, lane 4), confirming that it is similar in size to the δTCR glycoprotein on IDP2 cells (FIG. 2B, lane 2, open arrow).

To also compare δTCR polypeptide backbone sizes, cell surface $^{125}$I-labelled δTCR protein from MOLT-13 cells was digested with N-glycanase to remove asparagine-linked glycans (of the high mannose, hybrid, and complex-type; Tarentino et al., 1985, Biochem. 24:4665–4671; Hirani et al., 1987, Anal. Biochem. 162:485–492). The δTCR core polypeptides of MOLT-13 cells has a relative molecular mass of 35kD (FIG. 4B, lane 4), which is similar to that of the δTCR backbone of IDP2 cells (35Kd; described more fully in copending U.S. application Ser. No. 115,256, filed Oct. 29, 1987 now U.S. Pat. No. 5,024,940, issued Jun. 18, 1991, which is incorporated by reference in its entirety).

In addition, digestion of cell surface $^{125}$I-labelled MOLT-13 δTCR protein with endoglycosidase H (Endo H, removing only high mannose and certain hybrid N-glycans; Tarentino et al., 1974, J. Biol. Chem. 249:811–817; Trimble and Maley, 1984, Anal. Biochem. 141:514–522) caused a decrease in relative molecular mass of 2.5 kD, (FIG. 4B, lane 2) consistent with the presence of one carbohydrate moiety, leaving a relative mass of 2.5 kD of Endo H resistant carbohydrates attached to the polypeptide. Since there are two potential N-glycan attachment sites present in the δTCR constant domain (described more fully in copending U.S. application Ser. No. 115,256, filed Oct. 29, 1987, now U.S. Pat. No. 5,024,940 issued Jun. 18, 1991, which is incorporated by reference in its entirety; Loh et al., 1987, Nature 330:569–572), these data show that both are used, but that their N-glycans are processed differently, namely one as a high mannose N-glycan (Endo H-sensitive) and the other as a complex N-glycan (Endo H-resistant, but N-glycanase sensitive). In contrast to the different amounts of attached N-linked carbohydrate on γTCR polypeptide chains, the δTCR subunits expressed on PEER, IDP2 and MOLT-13 cells all revealed the same peptide core sizes and the presence of two N-linked glycans (FIG. 4B and data not shown).

6.2.6. T CELL RECEPTOR γδ COMPLEX, NOT ASSOCIATED WITH CD3, IS IDENTIFIED IN HUMAN ENDOMETRIAL GLANDULAR EPITHELIUM

In the early stages of placentation, infiltration of mononuclear cells is abundant at the proximity of spiral arteries and endometrial glands in maternal uterine tissues. These include an unusual population of T lineage cells of unknown function. Since many extravillous trophoblasts express a novel type of class I MHC antigens which is different from that expressed on most somatic cells, and a second T cell receptor (TCR) which consists of γ and δ chain has been proposed to function in non-MHC-restricted cytotoxicity. We have tested a panel of monoclonal antibodies to TCR γδ heterodimer (γδTCR) in pregnant & non-pregnant uteri. Surprisingly, γδTCR complex was not detected in leukocytes, but was localized in the cytoplasm of the endometrial glandular epithelium from pregnant uteri. These antibodies also reacted with the glandular epithelium from non-pregnant uteri, the reactivity was stronger in the secretory phase than that in the proliferative phase of menstrual cycle. However, the presence of TCR γδ complex was not associated with CD3 complex which was shown by using three different monoclonal antibodies to CD3 (OKT3, anti-leu-4, UCHT-1). The TCR γδ-positive glandular epithelial cells did not react with monoclonal antibodies to TCR αβ bearing endometrial glandular cells undergo, at least, phenotypic alterations under local regulation of gene expression.

6.3. DISCUSSION

In this example, three protein forms of the human γTCR glycoprotein are compared, namely the disulfide-linked 40kD γTCR (Form 1), the nondisulfide-linked 55kD γTCR (Form abc) and the nondisulfide-linked 40kD γTCR protein (Form 2bc). All three forms are shown to be associated with a γTCR subunit. Complementary DNA sequences representing the first two γTCR forms have been reported previously (Krangel et al., 1987, supra; Littman et al., 1987, supra). The constant region of γTCR Form 1 (on PBL-C1) is encoded by the Form 2abc (on IDP2 and PEER cells) utilizes the Cγ2 gene segment containing CII exon copy a, copy b and copy c. The cDNA sequence corresponding to a γTCR chain of Form 2bc was shown to contain a Cγ2 gene segment utilizing only two CII exon copies, namely copy b and copy c. Similarly, it seems likely that the gene structure of the γTCR connector region of Clone II and PBL-L2 (nondisulfide-linked, 40kD γTCR protein) will also be like the MOLT-13 structure determined here, namely of Form 2bc. Since the δTCR constant region used is the same for all these forms (described more fully in copending U.S. application Ser. No. 115,256, filed Oct. 29, 1987, now U.S. Pat. No. 5,024,940, issued Jun. 18, 1991, which is incorporated by reference in its entirety; Loh et al., supra) a complete comparison of the structures of the three γδTCR forms in man now can be made (FIG. 7).

Two Cγ2 polymorphic genomic forms exist in man (Lefranc et al., 1986c, supra; Pellici et al., 1987, Science 237:1051–1055). The two transcript forms (Form 2abc and Form 2bc) are probably the product of these different allelic types. To date, no allelic form of γTCR polypeptides have been found in mice. We conclude that the dramatic difference in γTCR cell surface protein size between Form 2abc (55kD) and Form 2bc (40kD) is largely determined by the amount of attached N-link carbohydrates, most likely reflecting the number of N-linked glycans. Backbone sizes of IDP2 γTCR (Form 2abc) and MOLT-13 γTCR (Form 2bc) proteins have been measured to be 40kD and 35kD respectively, on the basis of SDS-PAGE, which correlates well with their predicted molecular masses of 36.6kD and 34.8kD respectively, calculated on the basis of cDNA sequences. It is clear that this small difference in backbone size (5kD in SDS-PAGE), accounted for mainly by one CII exon encoded peptide of 16 amino acids, contributed to, but could not solely explain the observed difference in molecular mass between the 55kD and 40kD nondisulfide-linked γTCR surface forms. Form 2abc γTCR polypeptides possess 5 potential N-linked glycan attachment sites that are probably all used, in contrast to the MOLT-13 γTCR polypeptide which bears one additional potential attachment site, while carrying only 2 to 3 N-linked glycans. The reason for this limited use of potential attachment sites is unknown, but may result from the influence of the CII exon encoded peptides on the conformation of the γTCR protein. The CII exon encoded peptides and their neighboring amino acids make up a connector region between the plasma membrane and the immunoglobulin-like constant domain. This region contains most of the N-linked glycan attachment sites (FIG. 8). We conclude that the CII exon copies appear to determine the protein form not only by determining polypeptide backbone size, and by creating the ability to disulfide-link chains, but also by influencing the amount of attached carbohydrates.

δTCR complementary DNAs of IDP2 (described more fully in copending U.S. application Ser. No. 115,256, filed Oct. 29, 1987, now U.S. Pat. No. 5,024,940, issued Jun. 18, 1991, which is incorporated by reference in its entirety), PEER (Loh et al., supra) and MOLT-13 (data not shown) cells have been sequenced and were found to be identical, except for the diversity/N-region interspacing the variable and constant region gene segments. The δTCR protein on WM-14 cells has a relative molecular mass of 43kD, which is similar to the δTCR protein described previously (Borst et al., 1987, Nature 325:683–688 and Lanier et al., 1987, J. Exp. Med. 165:1076–1094) but is 3kD larger than the other δTCR chains. These 43kD δTCR proteins might indicate the presence of an additional N-linked glycosylation site in a different Vδ variable domain.

Since structural differences comparable to those described for γTCR constant region segments have not been observed for αTCR and βTCR genes (Yoshikai et al., 1985, Nature 316:837–840; Toyonaga et al., 1985, Proc. Natl. Acad. Sci. U.S.A. 82:8624–8628; Royer et al., 1984, J. Exp. Med. 160:947–952; Kronenberg et al., 1985, Nature 313:647–653), the significance of the dramatic structural diversity of these three γ, δTCR forms in man remains a mystery. However, there is possible similarity in the number of human CII exon repeats with the length in murine Cγ regions, of which the Cγ1, Cγ2 and Cγ4 constant regions encode for 15, 10 and 33 amino acid connector region respectively (Garman et al, 1986, Cell 45:733–742; Iwamoto et al., 1986, J. Exp. Med. 163:1203–1212). The connector regions in mouse, however, reflect a difference in the size of the relevant exon, not the multiple use of exons as is seen in Form 2abc γTCR and Form 2bc γTCR in humans. Also, the murine γTCR only exist in disulfide linked forms in contrast to the two nondisulfide linked human forms.

Importantly, the human γ, δTCR forms do not appear to be used equally. In some individuals (selected for high percentages of γ, δTCR lymphocytes) a single form (Form 1) predominates, suggesting that either positive selection occurs for this form or that there is selection against other γ, δTCR forms. The mechanism(s) responsible for preferential usage of the γδTCR forms remains to be determined. Such structural diversity and preferential usage may prove relevant to functional differences in these γ, δTCR complexes in various normal or abnormal disease states.

7. EXAMPLE: CHARACTERIZATION OF A HUMAN δ-T CELL RECEPTOR GENE AND A Vδ SPECIFIC MONOCLONAL ANTIBODY

7.1. MATERIALS AND METHODS

7.11. ISOLATION AND SEQUENCING OF AK119 δTCR cDNA CLONES

A cDNA library was generated from the PBL T-cell clone, AK119, by the method of Gubler and Hoffmann (Gubler and Hoffman, 1983, Gene 25:263). About 100,000 plaques of an amplified library were screened using a $^{32}$P-labelled nick-translated Cδ probe, isolated from a δTCR clone called 0–024 (described more fully in copending U.S. application Ser. No. 115,256, filed Oct. 29, 1987, now U.S. Pat. No. 5,024,940, issued Jun. 18, 1991, which is incorporated by reference in its entirety). The longest hybridizing cDNA clone (1.3kb clone C11963) was selected for sequence analysis by the dideoxy chain termination method.

7.1.2. CLONING A REARRANGED δTCR GENE

A 3.5 kb genomic DNA clone containing the rearranged Vδ gene was obtained from AK119 cells as follows. Eco RI digested DNA was size fractionated on a preparative agarose gel, ligated into λgt10, packaged and transfected into E. coli. Recombinant phage were screened with a $^{32}$P-labeled nick translated 550 bp Eco RI fragment derived from the cDNA clone, c11963. A rearranged clone called r11961 which contains a 0.8 kb Hinc II fragment (V region specific) and a 1 kb Hinc II-Eco RI fragment (V-J region) was isolated.

7.1.3. DNA PREPARATION

Fetal and newborn thymic tissues were collected in accordance with accepted guidelines regarding patients' rights and approval. T-cell clones were obtained from peripheral blood, pleural exudate or cerebrospinal fluid by limiting dilution and were cultured in vitro (Hafler et al., 1985, Ann Neurol. 18:451, Van de Griend et al., 1987, J. Immunol. 138:1627). In all cases DNA was prepared by digestion with proteinase K in 1% sodium dodecyl sulfate, followed by extraction with phenol/chloroform and ethanol precipitation.

7.1.4. SOUTHERN BLOT ANALYSIS

Genomic DNA was digested with Eco RI, size fractionated on a 0.9% agarose gel and transferred to nitrocellulose. Hybridization was carried out with $^{32}$P-nick translated probes as previously described (Maniatis, 1982, Molecular Cloning: A Laboratory Manual (Cold Spring Harbor Laboratory; Cold Spring Harbor, New York).

7.1.5. CYTOFLUOROMETRIC ANALYSIS

Normal peripheral blood monoclear cells (PBMC), obtained from volunteers were isolated by fractionation on a Ficoll gradient. PBMC and PBL T-cell clones were stained by indirect immunofluorescence using TCS-δ1 mAb referred to previously as δTCAR3 and fluorescein-conjugated goat antimouse IgG (Becton Dickinson) and analyzed in a fluorescence activated flow cytometer.

7.2. RESULTS

7.2.1. DIVERSITY OF δTCR GENE REARRANGEMENTS

Using a Cδ probe, we isolated a 1.3 kb δTCR cDNA clone, termed c119δ3, from a λgt10 cDNA library of the T-cell clone AK119. The 5' end of c119δ3 was sequenced and found to use previously identified Vδ and Jδ genes (described more fully in U.S. application Ser. No. 115,256, filed Oct. 29, 1987, now U.S. Pat. No. 5,024,940, issued Jun. 18, 1991, which is incorporated by reference in its entirety and Loh et al., 1987, supra). The sequence of the V-J junction indicated that C119δ3 has an in frame V-J joint.

A 550 basepair (bp) Eco RI fragment encoding all the variable and joining regiona and part of the constant region (V-J-C probe) was obtained from c119δ3 and used in Southern blot analysis of Eco RI digested genomic DNA from AK119. This probe detects a germline 3.2 kb Vδ and a germline 1.0 kb Cδ band. AK119 showed an extra rearranged 3.5 kb band that is identical to the common δTCR rearrangement (described more fully in, copending U.S. application Ser. No. 115,256, filed Oct. 29, 1987, now U.S. Pat. No. 5,024,940, issued Jun. 18, 1991, which is incorporated by reference in its entirety and Loh et al., 1987, supra) (rearrangement II in FIG. 9). This 3.5 kb band was cloned from a Eco RI size-fractionated λgt10 genomic library using the V-J-C cDNA probe. A partial map of the cloned rearranged δTCR gene, called r119δ1, is shown in FIG. 8. The localization of the variable and joining region was determined using J oligonucleotide probes and variable region specific probes. From r119δ1, a 1 kb V-J probe was isolated by digestion with Hinc II and Eco RI enzymes (see FIG. 8).

This V-J probe was used to determine the diversity of δTCR gene rearrangements in a panel of 13 human γ-δTCR positive T-cell clones and 3 human γ-δTCR positive tumor cell lines. As shown in FIG. 9, five common rearrangements, numbered I-V, are seen in the polyclonal newborn thymocyte sample (lane 11). These rearrangements are representative of rearrangements used by the human T cell clones. Only rearrangement II hybridizes to the Hinc II - Hinc II Vδ specific probe (data not shown). Although we do not know that all these rearrangements represent V-D-J rather than D-J rearrangements, some of them must represent rearrangements of new variable regions to the previously characterized Jδ gene segment because these cells express a functional δTCR polypeptide chain on their cell surfaces. We have not ruled out the possibility that these new rearrangements represent rearrangements of a single new Vδ gene to other Jδ genes, yet to be identified. Our data is consistent with the fact that there must be 2-5 variable region genes that can be used in δTCR gene rearrangements.

7.2.2. DETERMINING THE SPECIFICITY OF mAb TCSδ-1

δTCS-1, previously referred to as δTCAR-3 was generated by fusing splenocytes from of mice immunized with the human tumor γ-δcell line MOLT-13 with a mouse myeloma line. When used in fluorescent activated cell sorter analysis, δTCS-1 reacted only with some but not all human γ-δT cells. The results are given in Table 1. There is a perfect correlation with usage of the AK119 Vδ gene (rearrangement II) with positive staining by δTCS1. This data provides strong evidence that the epitope recognized by δTCSI is encoded in the AK119 Vδ gene or in combinatorial epitope of the rearranged AK119Vδ-Jδ gene.

TABLE 1

Correlation between staining by TCS-δ1 MAb and a specific Vδ rearrangement

| | δ rearrangement[1] | δTCS1 |
|---|---|---|
| human γ-δ T cell clones | | |
| AK4 | V/?[2] | −[4] |
| AK615 | I/IV | − |
| AK925 | III/? | nd |
| 1004 | I/IV | − |
| 1005 | I/IV | − |
| 1011 | I/IV | − |
| 1012 | I/IV | − |
| 1015 | I/? | − |
| 1018 | IV/? | − |
| Wi.1 | I/? | − |
| 1019 | II/IV | nd |
| AK119 | II/? | + |
| Wi.K | II/III | + |
| human γ-δ T-cell tumor lines | | |
| Peer | II/? | + |
| Molt-13 | II/V | + |
| DND41 | II/VI[3] | + |

[1] δTCR rearrangements detected with V-J probe, numbered I-V as in FIG. 9.
[2] Only 1 rearrangement was identified in each case even though no germline Jδ was detected.
[3] A new rearrangement is observed which is not seen in newborn or fetal thymocytes. This rearrangement has been assigned rearrangement VI.
[4] + means positive staining, − means negative staining. nd means not determined.

7.3. DISCUSSION

The direct correlation between the usage of the AK119 Vδ gene (namely the rearranged 3.5 kb fragment or rearrangement II) and staining by δTCSI provides evidence that the δTCSI epitope is encoded in the AK119 Vδ gene or in a combinatorial Vδ-Kδ regions. This is the first Vδ or Vδ-Jδ specific map that can be used to stain cell surface δTCRs. The generation of variable region specific mAbs is useful for studying the usage of Vδ genes in different tissues, during different stages of development, and in disease. Studies in the murine system have suggested preferential usage of the most 3' Vδ gene in the TCR-δ locus in the fetal thymus (Chien et al., 1987, supra).

Our studies have also shown that the repertoire of the TCR-δ gene is not as restricted as previously described in copending U.S. application Ser. No. 115,256, filed Oct. 29, 1987, now U.S. Pat. No. 5,024,940, issued Jun. 18, 1991, which is incorporated by reference in its entirety and Loh et al., 1987, supra. Five common rearrangements have been demonstrated in this paper. In addition, since only one rearrangement was detected in some of the γ-δ T-cell clones which did not show the germline Jδ band, these clones probably have rearrangements to other Jδ genes that are not detected by our Jδ probe. Future studies will focus on characterizing the different TCR-δ gene rearrangements in detail. An understanding of the repertoire of the γ-δ TCRs will provide insight into antigen specificity and the role of human γ-δ T cells in normal and abnormal disease states.

Hybridomas 5A6.E9, producing monoclonal antibody anti-TCR δ1, and #3, producing monoclonal antibody Cγm1, have been deposited with the American Type Culture Collection, 12307 Parklawn Drive, Rockville, Maryland 20852 under the provisions of the Budapest Treaty On the International Recognition of the Deposit of Microorganisms for the Purposes of Patent Procedure, and have been assigned accession numbers HB 9772 and HB 9773, respectively.

What is claimed is:

1. A method for diagnosing an immune system abnormality in a human subject which comprises:
   a) determining in a sample from the subject the number of T cells which have a Form 1 δ chain of a T cell antigen receptor;
   b) determining in a sample from the subject the number of T cells which have a surface marker selected from the group consisting of Form 2abc γ chain of a T cell antigen receptor, and Form 2bc γ chain of a T cell antigen receptor;
   c) determining the ratio of the number of T cells in step (a) to the number of T cells in step (b); and
   d) comparing the ratio determined in step (c) to the ratio determined in a sample from a subject who does not have the immune abnormality, where a difference in the ratios so determined is indicative of the immune system abnormality.

2. A method for diagnosing an immune system abnormality in a human subject which comprises:
   a) determining in a sample from the subject the number of T cells which have a Form 2abc γ chain of a T cell antigen receptor;
   b) determining in a sample from the subject the number of T cells which have a surface marker selected from the group consisting of Form 1 γ chain of a T cell antigen receptor, and Form 2bc γ chain of a T cell antigen receptor;
   c) determining the ratio of the number of T cells in step (a) to the number of T cells in step (b); and
   d) comparing the ratio determined in step (c) to the ratio determined in a sample from a subject who does not have the immune abnormality,
   where a difference in the ratios so determined is indicative of the immune system abnormality.

3. A method for diagnosing an immune system abnormality in a human subject which comprises:
   a) determining in a sample from the subject the number of T cells which have a Form 2bc γ chain of a T cell antigen receptor;
   b) determining in a sample from the subject the number of T cells which have a surface marker selected from the group consisting of Form 2abc γ chain of a T cell antigen receptor, and Form 1 γ chain of a T cell antigen receptor;
   c) determining the ratio of the number of T cells in step (a) to the number of T cells in step (b); and
   d) comparing the ratio determined in step (c) to the ratio determined in a sample from a subject who does not have the immune abnormality,
   where a difference in the ratios so determined is indicative of the immune system abnormality.

4. A method for diagnosing an immune system abnormality in a human subject which comprises:
   a) determining in a sample from the subject the number of T cells which have a T cell antigen receptor having a Form 1 γ chain and a δ chain;
   b) determining in a sample from the subject the number of T cells which have a surface marker selected from the group consisting of a T cell antigen receptor having a Form 2abc γ chain and a δ chain, and a T cell antigen receptor having of a Form 2bc γ chain and a δ chain;
   c) determining the ratio of the number of T cells in step (a) to the number of T cells in step (b); and
   d) comparing the ratio determined in step (c) to the ratio determined in a sample from a subject who does not have the immune system abnormality.
   where a difference in the ratios so determined is indicative of the immune system abnormality.

5. A method for diagnosing an immune system abnormality in a human subject which comprises:
   a) determining in a sample from the subject the number of T cells which have a T cell antigen receptor having a Form 2abc γ chain and a δ chain;
   b) determining in a sample from the subject the number of T cells which have a surface marker selected from the group consisting of a T cell antigen receptor having a Form 1 γ chain and a δ chain, and a T cell antigen receptor having a Form 2bc γ chain and a δ chain;
   c) determining the ratio of the number of T cells in step (a) to the number of T cells in step (b); and
   d) comparing the ratio determined in step (c) to the ratio determined in a sample from a subject who does not have the immune abnormality,
   where a difference in the ratios so determined is indicative of the immune system abnormality.

6. A method for diagnosing an immune system abnormality in a human subject which comprises:
   a) determining in a sample from the subject the number of T cells which have a T cell antigen receptor having a Form 2bc γ chain and a δ chain;
   b) determining in a sample from the subject the number of T cells which have a surface marker selected from the group consisting of a T cell antigen receptor having a Form 2abc γ chain and a δ chain, and a T cell antigen receptor having a Form 1 γ chain and a δ chain;
   c) determining the ratio of the number of T cells in step (a) to the number of T cells in step (b); and
   d) comparing the ratio determined in step (c) to the ratio determined in a sample from a subject who does not have the immune abnormality,
   where a difference in the ratios so determined is indicative of the immune system abnormality.

7. A method for diagnosing an immune system abnormality in a human subject which comprises:
   a) determining in a sample from the subject the amount of a Form 1 γ chain of a T cell antigen receptor;
   b) determining in a sample from the subject the amount of a surface marker selected from the group consisting of Form 2abc γ chain of a T cell antigen receptor, and Form 2bc γ chain of a T cell antigen receptor;
   determining the ratio of the amount in step (a) to the amount in step (b); and
   c) comparing the ratio determined in step (c) to the ratio determined in a sample from a subject who does not have the immune abnormality, where a difference in the ratios so determined is indicative of the immune system abnormality.

8. A method for diagnosing an immune system abnormality in a human subject which comprises:
   a) determining in a sample from the subject the amount of a Form 2abc γ chain of a T cell antigen receptor;
   b) determining in a sample from the subject the amount of a surface marker selected from the group consisting of Form 1 γ chain of a T cell antigen receptor, and Form 2bc γ chain of a T cell antigen receptor;

c) determining the ratio of the amount in step (a) to the amount in step (b); and
d) comparing the ratio determined in step (c) to the ratio determined in a sample from a subject who does not have the immune abnormality, where a difference in the ratios so determined is indicative of the immune system abnormality.

9. A method for diagnosing an immune system abnormality in a human subject which comprises:
   a) determining in a sample from the subject the amount of a Form 2bc γ chain of a T cell antigen receptor;
   b) determining in a sample from the subject the amount of a surface marker selected from the group consisting of Form 2abc γ chain of a T cell antigen receptor, and Form 1 γ chain of a T cell antigen receptor;
   c) determining the ratio of the amount in step (a) to the amount in step (b); and
   d) comparing the ratio determined in step (c) to the ratio determined in a sample from a subject who does not have the immune abnormality, where a difference in the ratios so determined is indicative of the immune system abnormality.

10. A method for diagnosing an immune system abnormality in a human subject which comprises:
    a) determining int he sample from the subject the amount of a T cell antigen receptor having a Form 1 γ chain and a δ chain;
    b) determining in a sample from the subject the amount of a surface marker selected from the group consisting of a T cell antigen receptor having a Form 2abc γ chain and a δ chain, and a T cell antigen receptor having a Form 2bc γ chain and a δ chain;
    c) determining the ratio of the amount in step (a) to the amount in step (b); and
    d) comparing the ratio determined in step (c) to the ratio determined in a sample from a subject who does not have the immune abnormality, where a difference in the ratios so determined is indicative of the immune system abnormality.

11. A method for diagnosing an immune system abnormality in a human subject which comprises;
    a) determining in a sample from the subject the amount of a T cell antigen receptor having a Form 2abc γ chain and a δ chain;
    b) determining in the sample from the subject the amount of a surface marker selected from the group consisting of a T cell antigen receptor having a Form 1 γ chain and a δ chain, and a T cell antigen receptor having a Form 2bc γ chain and a δ chain;
    c) determining the ratio of the amount in step (a) to the amount in step (b); and
    d) comparing the ratio determined in step (c) to the ratio determined in a sample from a subject who does not have the immune abnormality, where a difference in the ratios so determined is indicative of the immune system abnormality.

12. A method for diagnosing an immune system abnormality in a human subject which comprises:
    a) determining in a sample from the subject the amount of a T cell antigen receptor having a Form 2bc γ chain and a δ chain;
    b) determining in a sample from the subject the amount of a surface marker selected from the group consisting of a T cell antigen receptor having a Form 2abc γ chain and a δ chain, and a T cell antigen receptor having a Form 1 γ chain and a δ chain;
    c) determining the ratio of the amount in step (a) to the amount in step (b); and
    d) comparing the ratio determined in step (c) to the ratio determined in a sample from a subject who does not have the immune abnormality, where a difference in the ratios so determined is indicative of the immune system abnormality.

13. The method according to claim 1 in which step (a) comprises:
    (i) staining such T cells with an antibody to the Form 1γ chain under conditions that allow specific binding; and
    (ii) quantifying the number of cells stained; and in which step (b) comprises:
    (i) staining such T cells with an antibody to the surface marker under conditions that allow specific binding; and
    (ii) quantifying the number of cells stained.

14. The method according to claim 13 in which the quantifying is a method selected from the group consisting of fluorescence activated cell sorting and autoradiography.

15. The method according to claim 2 in which step (a) comprises:
    (i) staining such T cells with an antibody to the Form 2acbγ chain under conditions that allow specific binding; and
    (ii) quantifying the number of cells stained; and in which step (b) comprises:
    (i) staining such T calls with an antibody to the surface marker under conditions that allow specific binding; and
    (ii) quantifying the number of cells stained.

16. The method according to claim 15 in which the quantifying is a method selected from the group consisting of fluorescence activated cell sorting and autoradiography.

17. The method according to claim 3 in which step (a) comprises:
    (i) staining such T cells with an antibody to the Form 2bcγ chain under conditions that allow specific binding; and
    (ii) quantifying the number of cells stained; and in which step (b) comprises:
    (i) staining such T cells with an antibody to the surface marker under conditions that allow specific binding; and
    (ii) quantifying the number of cells stained.

18. The method according to claim 17 in which the quantifying is a method selected from the group consisting of fluorescence activated cell sorting and autoradiography.

19. The method according to claim 4 in which step (a) comprises:
    (i) staining such T cells with an antibody to the Form 1γ chain under conditions that allow specific binding; and
    (ii) quantifying the number of cells stained; and in which step (b) comprises:
    (i) staining such T cells with an antibody to the surface marker under conditions that allow specific binding; and
    (ii) quantifying the number of cells stained.

20. The method according to claim 19 in which the quantifying is a method selected from the group consisting of fluorescence activated cells sorting and autoradiography.

21. The method according to claim 5 in which step (a) comprises:
 (i) staining such T cells with an antibody to the Form 2abcγ chain under conditions that allow specific binding; and
 (ii) quantifying the number of cells stained; and in which step (b) comprises:
 (i) staining such T cells with an antibody to the surface marker under conditions that allow specific binding; and
 (ii) quantifying the number of cells stained.

22. The method according to claim 21 in which the quantifying is a method selected from the group consisting of fluorescence activated cell sorting and autoradiography.

23. The method according to claim 6 in which step (a) comprises:
 (i) staining such T cells with an antibody to the Form 2bcγ chain under conditions that allow specific binding; and
 (ii) quantifying the number of cells stained; and in which step (b) comprises:
 (i) staining such T cells with an antibody to the surface marker under conditions that allow specific binding; and
 (ii) quantifying the number of cells stained.

24. The method according to claim 23 in which the quantifying is a method selected from the group consisting of fluorescence activated cell sorting and autoradiography.

25. The method according to claim 1 in which the immune system abnormality is selected from the group consisting of cancer, acquired immune deficiency syndrome, congenital immunodeficiency, and autoimmune disease.

26. The method according to claim 2 in which the immune system abnormality is selected from the group consisting of cancer, acquired immune deficiency syndrome, congenital immunodeficiency, and autoimmune disease.

27. The method according to claim 3 in which the immune system abnormality is selected from the group consisting of cancer, acquired immune deficiency syndrome, congenital immunodeficiency, and autoimmune disease.

28. The method according to claim 4 in which the immune system abnormality is selected from the group consisting of cancer, acquired immune deficiency syndrome, congenital immunodeficiency, and autoimmune disease.

29. The method according to claim 5 in which the immune system abnormality is selected from the group consisting of cancer, acquired immune deficiency syndrome, congenital immunodeficiency, and autoimmune disease.

30. The method according to claim 6 in which the immune system abnormality is selected from the group consisting of cancer, acquired immune deficiency syndrome, congenital immunodeficiency, and autoimmune disease.

31. The method according to claim 7 in which the immune system abnormality is selected from the group consisting of cancer, acquired immune deficiency syndrome, congenital immunodeficiency, and autoimmune disease.

32. The method according to claim 8 in which the immune system abnormality is selected from the group consisting of cancer, acquired immune deficiency syndrome, congenital immunodeficiency, and autoimmune disease.

33. The method according to claim 9 in which the immune system abnormality is selected from the group consisting of cancer, acquired immune deficiency syndrome, congenital immunodeficiency, and autoimmune disease.

34. The method according to claim 10 in which the immune system abnormality is selected from the group consisting of cancer, acquired immune deficiency syndrome, congenital immunodeficiency, and autoimmune disease.

35. The method according to claim 11 in which the immune system abnormality is selected from the group consisting of cancer, acquired immune deficiency syndrome, congenital immunodeficiency, and autoimmune disease.

36. The method according to claim 12 in which the immune system abnormality is selected from the group consisting of cancer, acquired immune deficiency syndrome, congenital immunodeficiency, and autoimmune disease.

37. The method according to claim 1 in which the immune system abnormality is a cancer selected from the group consisting of leukemia and lymphoma.

38. The method according to claim 2 in which the immune system abnormality is a cancer selected from the group consisting of leukemia and lymphoma.

39. The method according to claim 3 in which the immune system abnormality is a cancer selected from the group consisting of leukemia and lymphoma.

40. The method according to claim 2 in which the immune system abnormality is a cancer selected from the group consisting of leukemia and lymphoma.

41. The method according to claim 5 in which the immune system abnormality is a cancer selected from the group consisting of leukemia and lymphoma.

42. The method according to claim 6 in which the immune system abnormality is a cancer selected from the group consisting of leukemia and lymphoma.

43. The method according to claim 7 in which the immune system abnormality is a cancer selected from the group consisting of leukemia and lymphoma.

44. The method according to claim 8 in which the immune system abnormality is a cancer selected from the group consisting of leukemia and lymphoma.

45. The method according to claim 9 in which the immune system abnormality is a cancer selected from the group consisting of leukemia and lymphoma.

46. The method according to claim 10 in which the immune system abnormality is a cancer selected from the group consisting of leukemia and lymphoma.

47. The method according to claim 11 in which the immune system abnormality is a cancer selected from the group consisting of leukemia and lymphoma.

48. The method according to claim 12 in which the immune system abnormality is a cancer selected from the group consisting of leukemia and lymphoma.

* * * * *